United States Patent
Sakamoto et al.

(10) Patent No.: US 10,696,895 B2
(45) Date of Patent: Jun. 30, 2020

(54) ACRYLIC ACID CROSSLINKED POLYMER AND USE THEREOF

(71) Applicant: NIPPON SHOKUBAI CO., LTD., Osaka-shi, Osaka (JP)

(72) Inventors: Shigeru Sakamoto, Himeji (JP); Kozo Nogi, Himeji (JP); Tomoyuki Arake, Himeji (JP); Erina Minami, Himeji (JP); Shinichi Fujino, Himeji (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 108 days.

(21) Appl. No.: 15/748,266

(22) PCT Filed: Jul. 29, 2016

(86) PCT No.: PCT/JP2016/003524
§ 371 (c)(1),
(2) Date: Jan. 29, 2018

(87) PCT Pub. No.: WO2017/017964
PCT Pub. Date: Feb. 2, 2017

(65) Prior Publication Data
US 2018/0215993 A1    Aug. 2, 2018

(30) Foreign Application Priority Data
Jul. 29, 2015   (JP) ................................ 2015-149654

(51) Int. Cl.
C09K 8/68      (2006.01)
C08F 220/06   (2006.01)
(Continued)

(52) U.S. Cl.
CPC ............ *C09K 8/685* (2013.01); *C08F 220/06* (2013.01); *C09K 8/882* (2013.01); *C09K 8/887* (2013.01);
(Continued)

(58) Field of Classification Search
CPC ........ C09K 8/685; C09K 8/882; C09K 8/887; C08F 220/06
See application file for complete search history.

(56) References Cited

U.S. PATENT DOCUMENTS

| 4,914,170 A | 4/1990 | Chang et al. |
| 5,760,080 A | 6/1998 | Wada et al. |

(Continued)

FOREIGN PATENT DOCUMENTS

| JP | 58-015511 A | 1/1983 |
| JP | 01-165610 A | 6/1989 |

(Continued)

OTHER PUBLICATIONS

PCT/ISA/206 for PCT/JP2016/003524 dated Aug. 30, 2016.

*Primary Examiner* — Aiqun Li
(74) *Attorney, Agent, or Firm* — Dickinson Wright PLLC

(57) ABSTRACT

The present invention provides a novel acrylic acid crosslinked polymer and the use thereof. The present invention provides the acrylic acid crosslinked polymer in which the content of soluble components is 40 wt. % or higher. The present invention also provides a method for adjusting the viscosity of a fracturing fluid in a hydraulic fracturing method, the viscosity adjustment method including: A) a step of measuring the types and quantities of metal cations which are in water and which are the object of viscosity adjustment; B) a step of selecting the type and quantity of an acrylic acid crosslinked polymer on the basis of the types and quantities of metal cations and the pH so as to achieve a viscosity that is required for fracturing in a hydraulic fracturing method; and C) a step of adjusting the viscosity of the fracturing fluid using the acrylic acid crosslinked polymer of the selected type and quantity.

18 Claims, 18 Drawing Sheets

(51) Int. Cl.
*C09K 8/88* (2006.01)
*G01N 11/00* (2006.01)
*E21B 43/26* (2006.01)
*G01N 33/44* (2006.01)

(52) U.S. Cl.
CPC .......... *E21B 43/26* (2013.01); *G01N 33/442* (2013.01); *G01N 11/00* (2013.01)

(56) References Cited

U.S. PATENT DOCUMENTS

| | | |
|---|---|---|
| 6,054,541 A | 4/2000 | Wada et al. |
| 6,180,724 B1 | 1/2001 | Wada et al. |
| 2006/0041028 A1 | 2/2006 | Crews |
| 2006/0205605 A1 | 9/2006 | Dessinges et al. |
| 2009/0234314 A1 | 9/2009 | Nakamura et al. |
| 2009/0312183 A1* | 12/2009 | Fujimaru ............ A61L 15/24 502/402 |
| 2013/0213657 A1 | 8/2013 | Dobson, Jr. et al. |
| 2013/0288934 A1 | 10/2013 | Powell et al. |
| 2016/0060506 A1 | 3/2016 | Takahashi et al. |

FOREIGN PATENT DOCUMENTS

| | | |
|---|---|---|
| JP | 05-247221 A | 9/1993 |
| JP | 06-041534 A | 2/1994 |
| JP | 08-057310 A | 3/1996 |
| JP | 2009-520834 A | 5/2009 |
| WO | 2011040530 A1 | 4/2011 |
| WO | 2015068688 A1 | 5/2014 |
| WO | 2014162793 A1 | 10/2014 |

\* cited by examiner

[Figure 1]
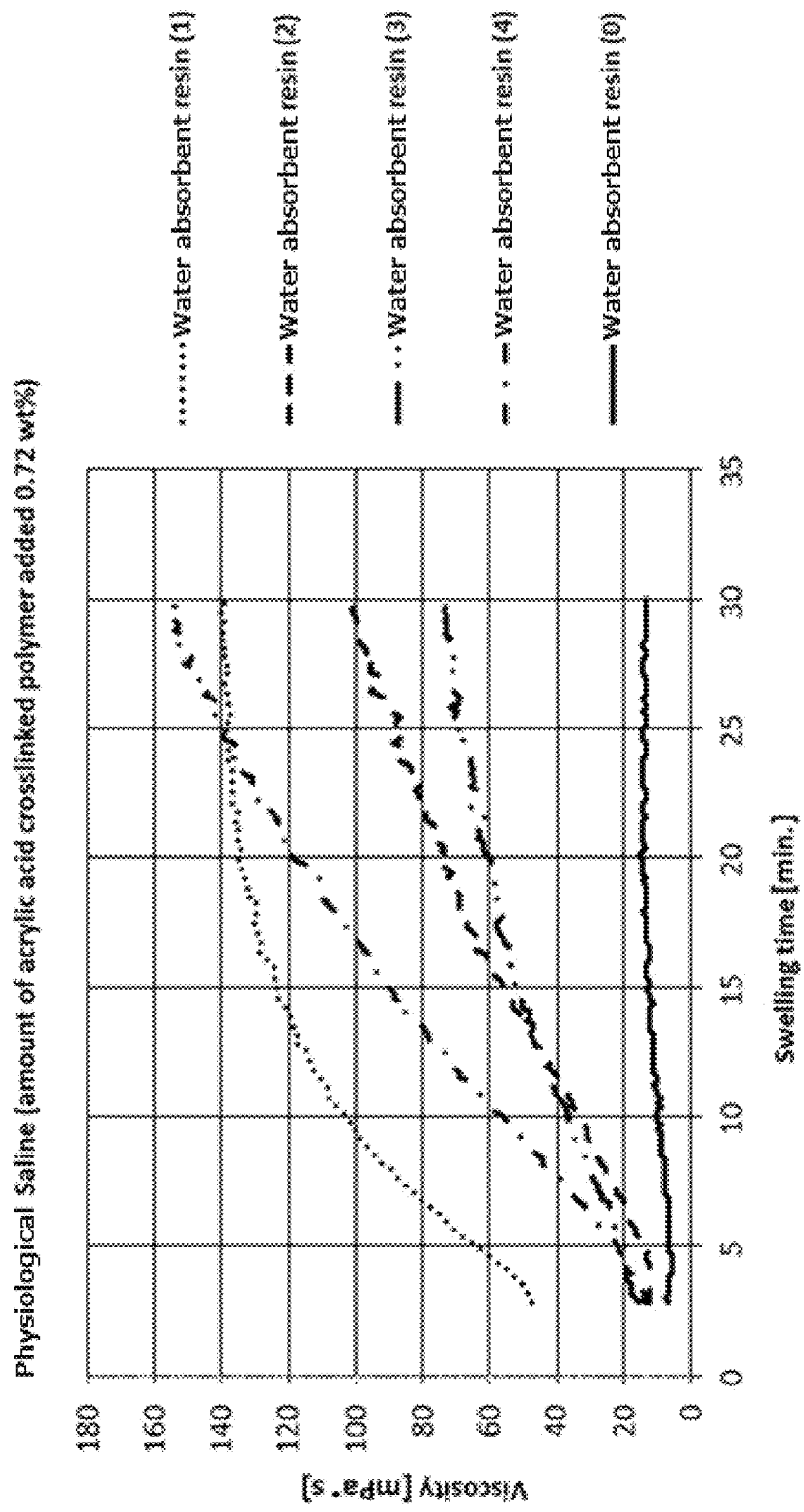

[Figure 2]
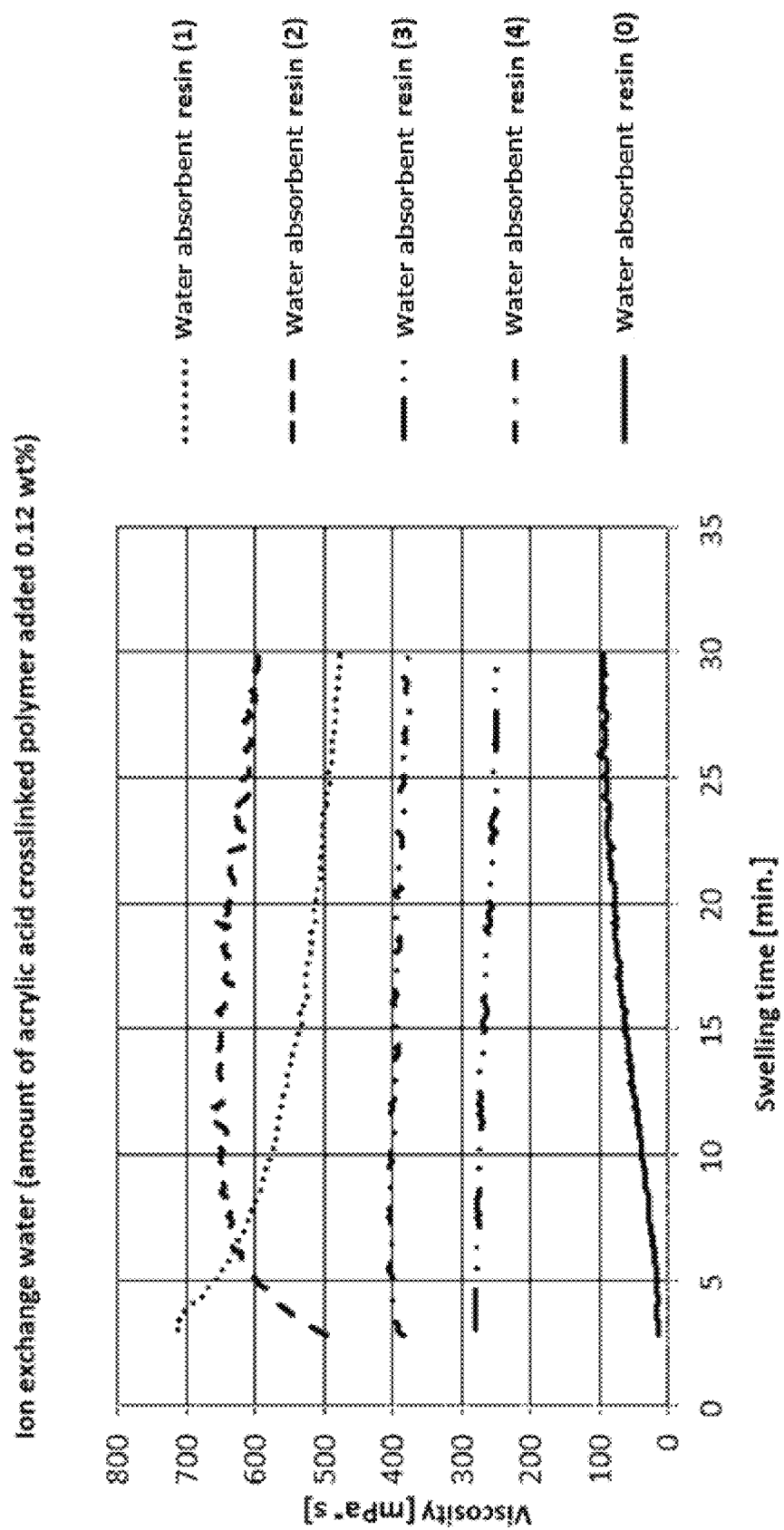

[Figure 3]
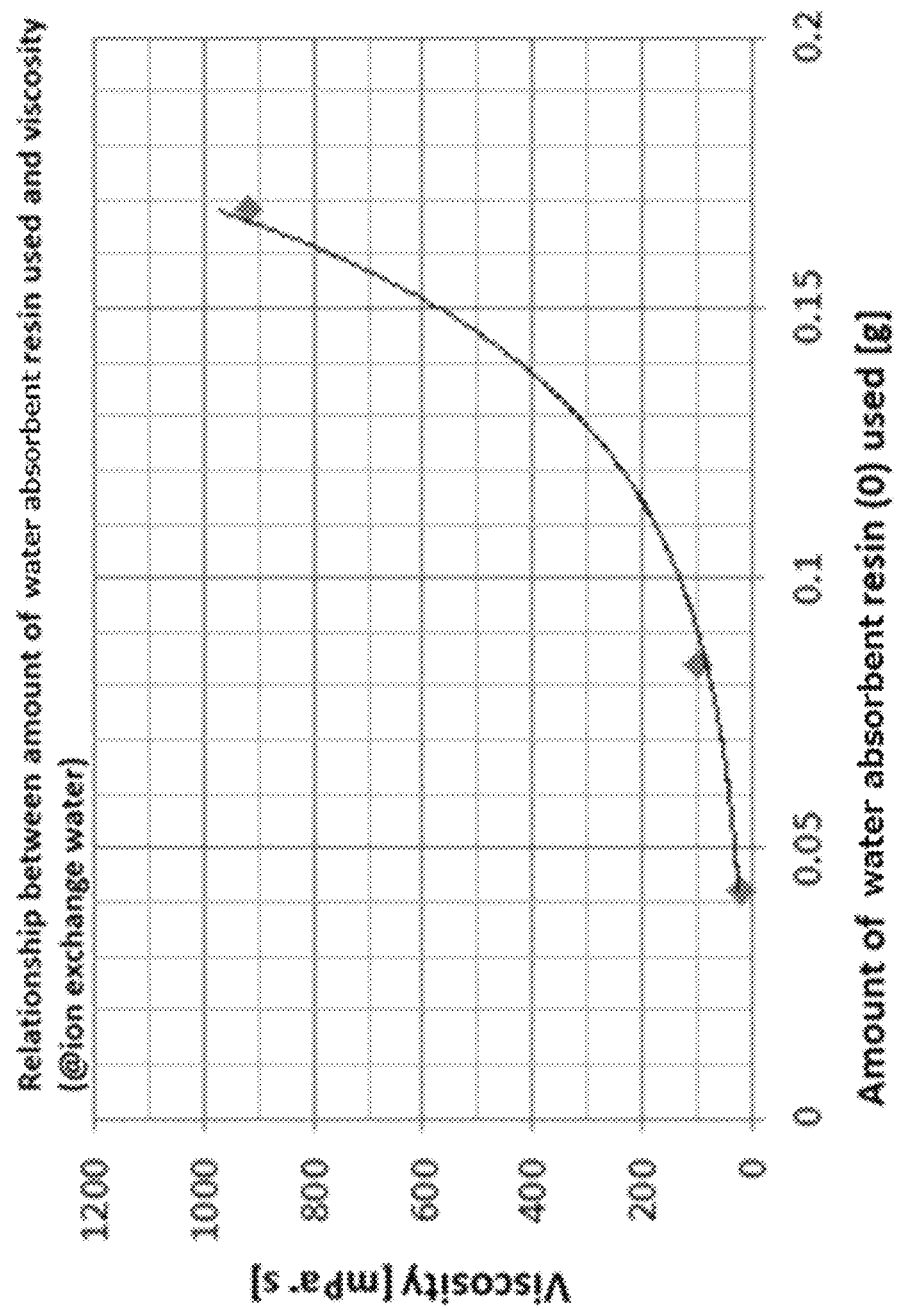

[Figure 4]
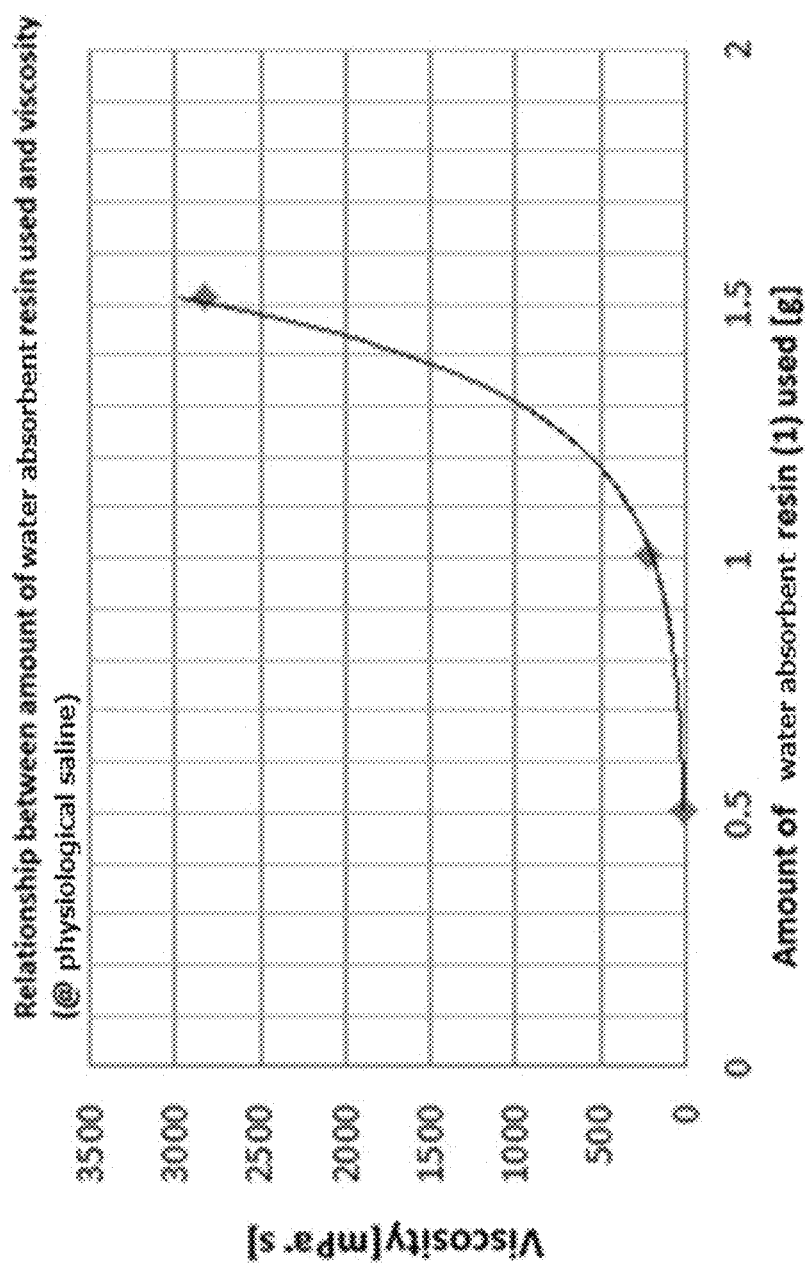

[Figure 5]
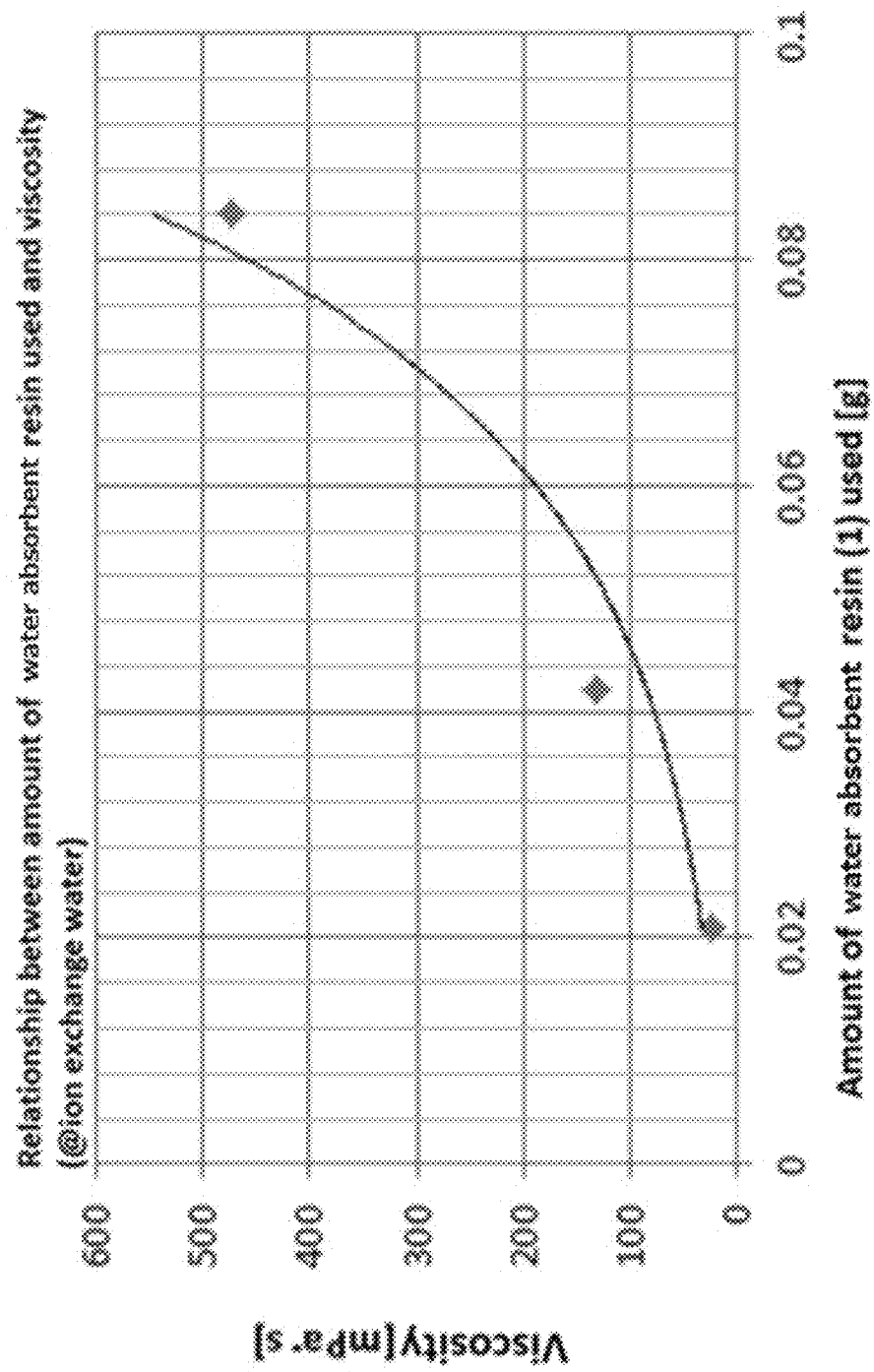

[Figure 6]
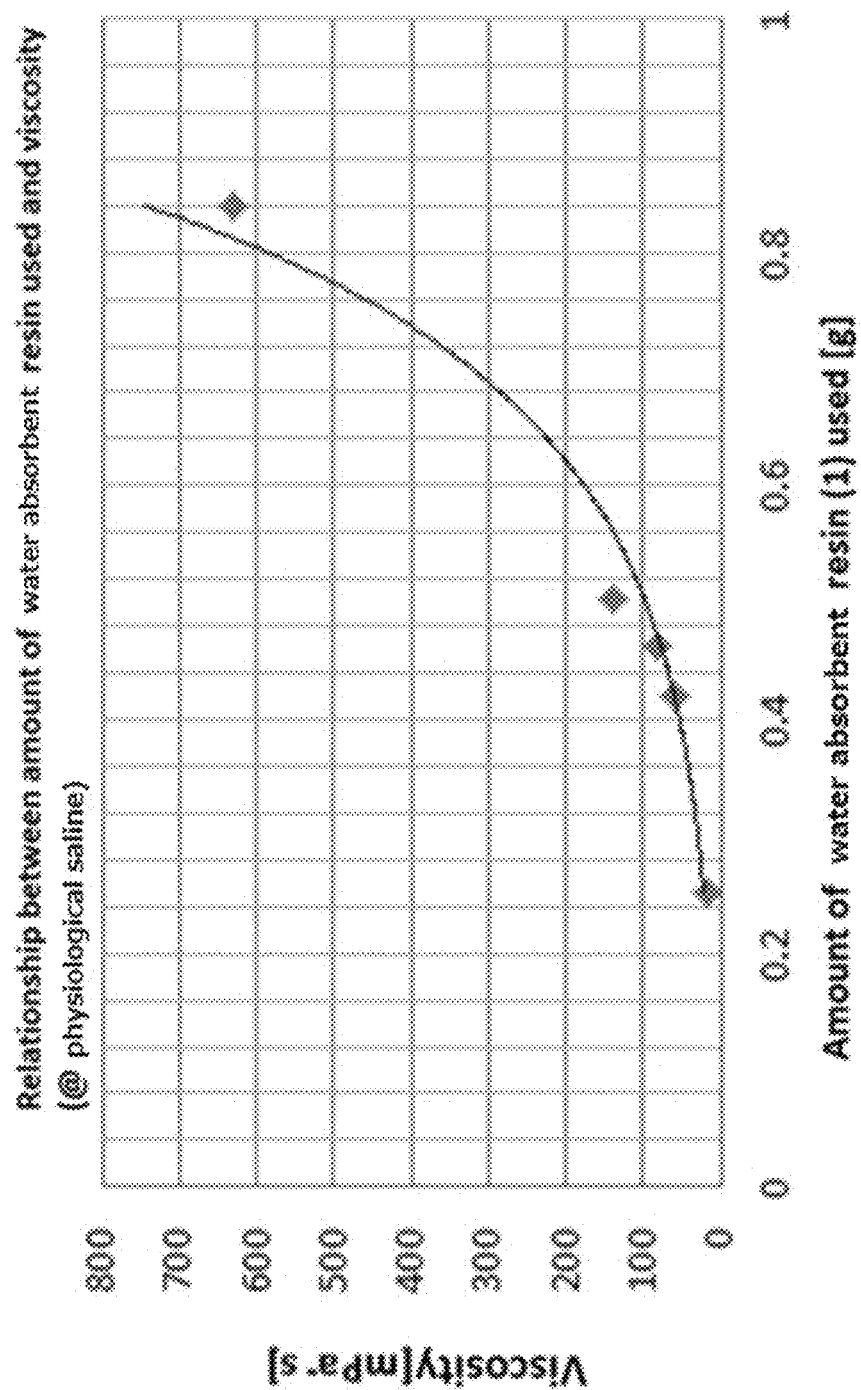

[Figure 7]
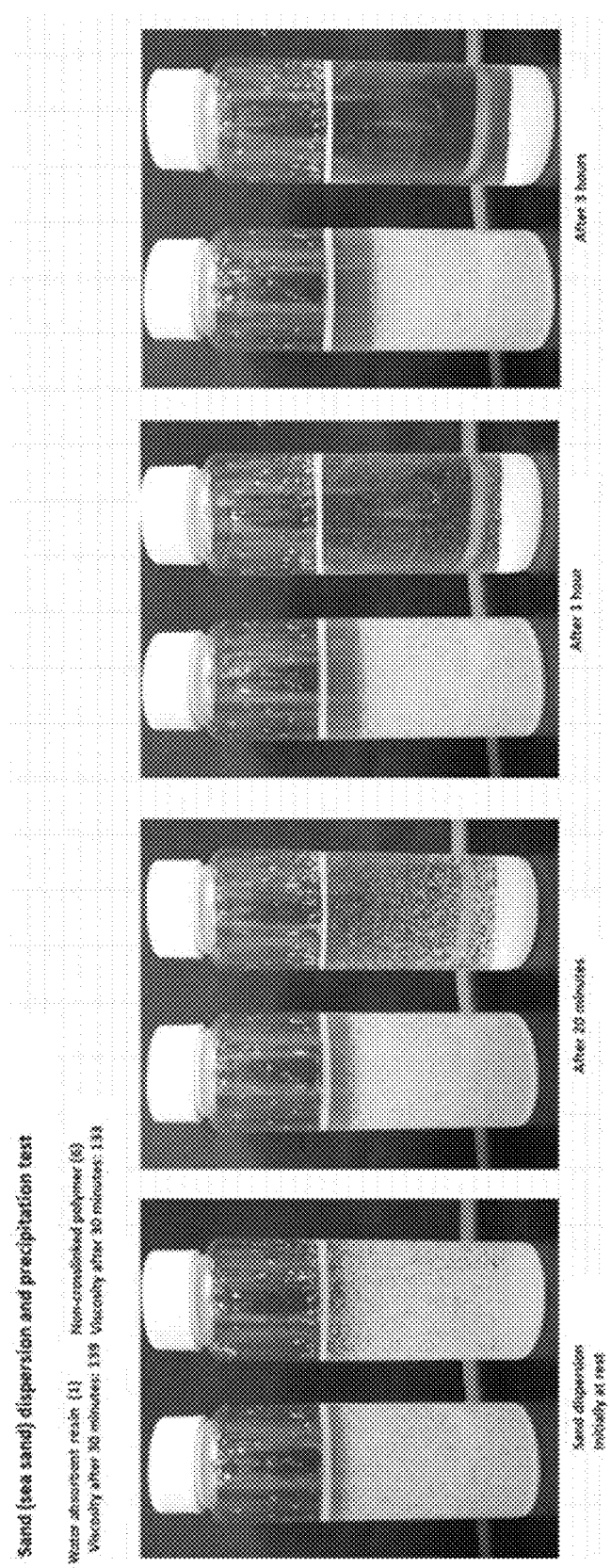

[Figure 8]
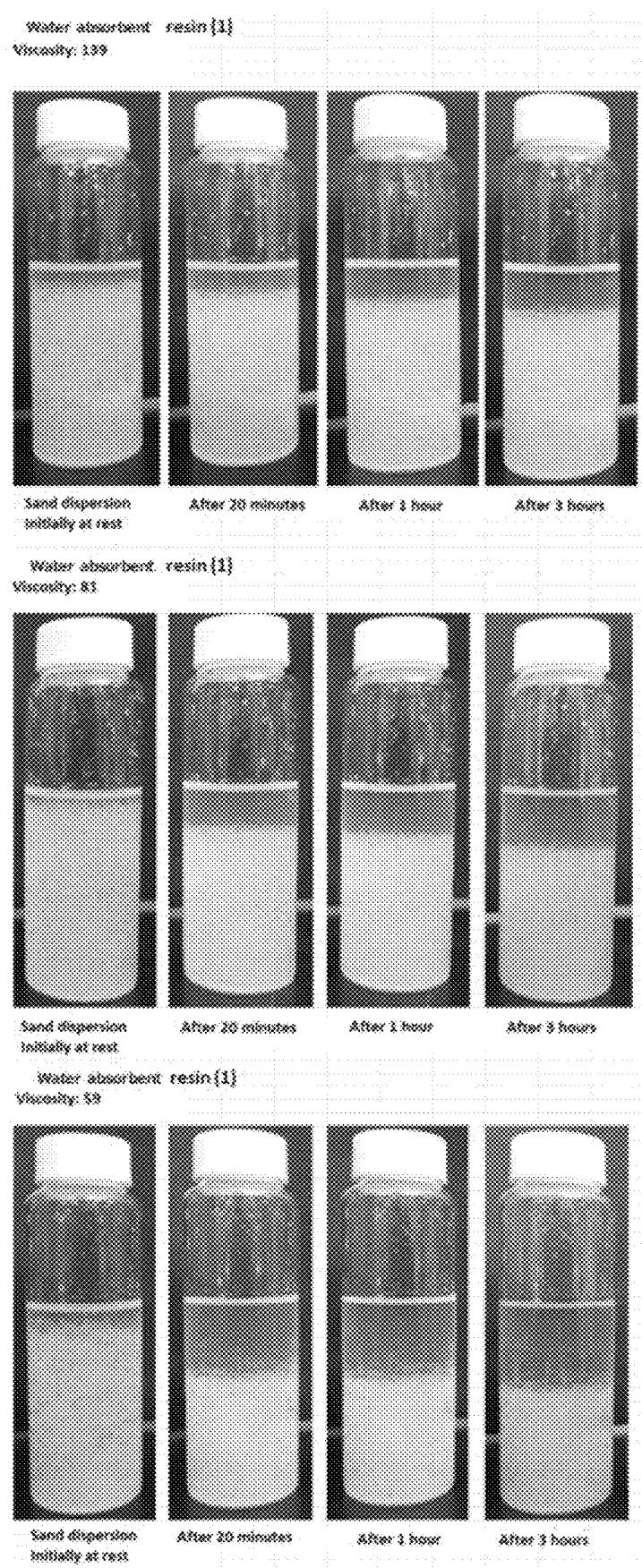

[Figure 9]
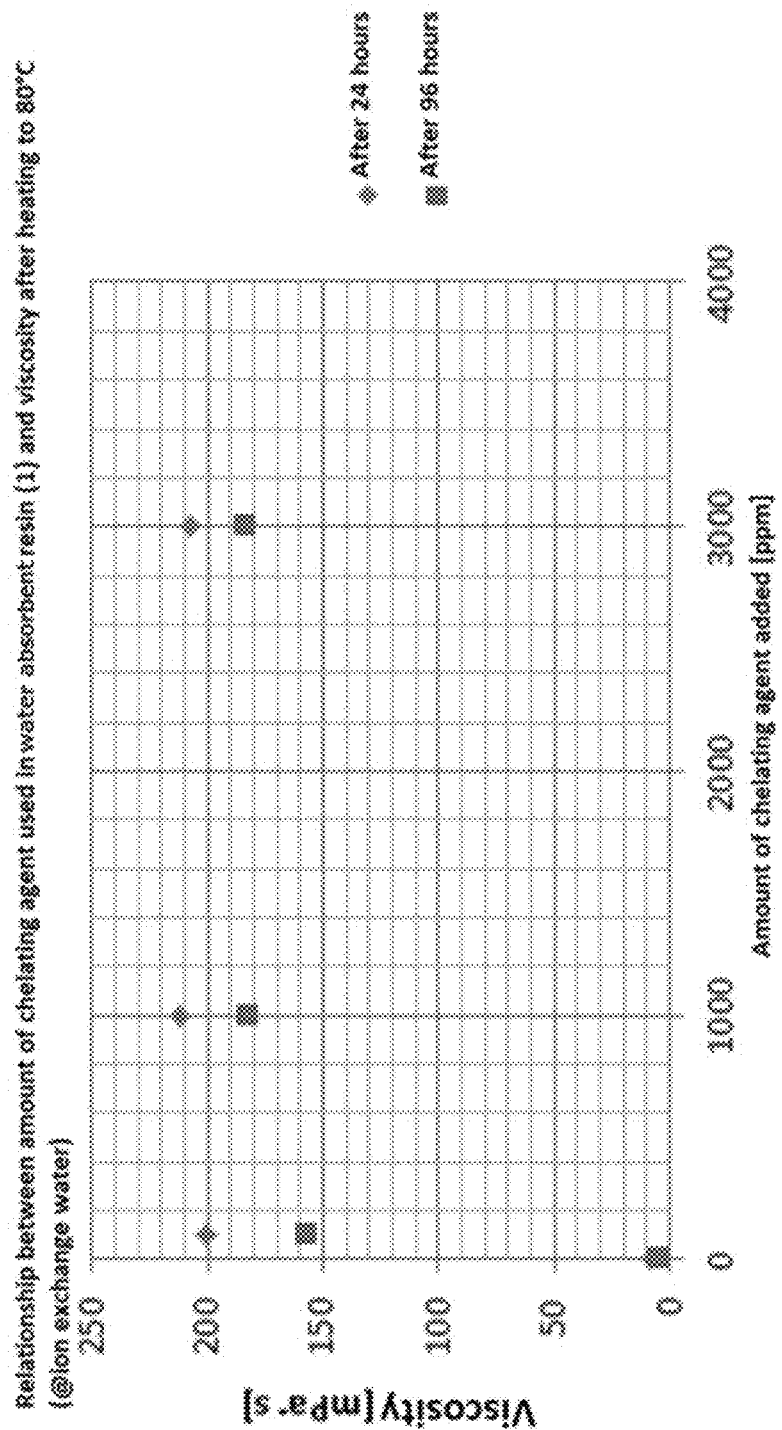

[Figure 10]
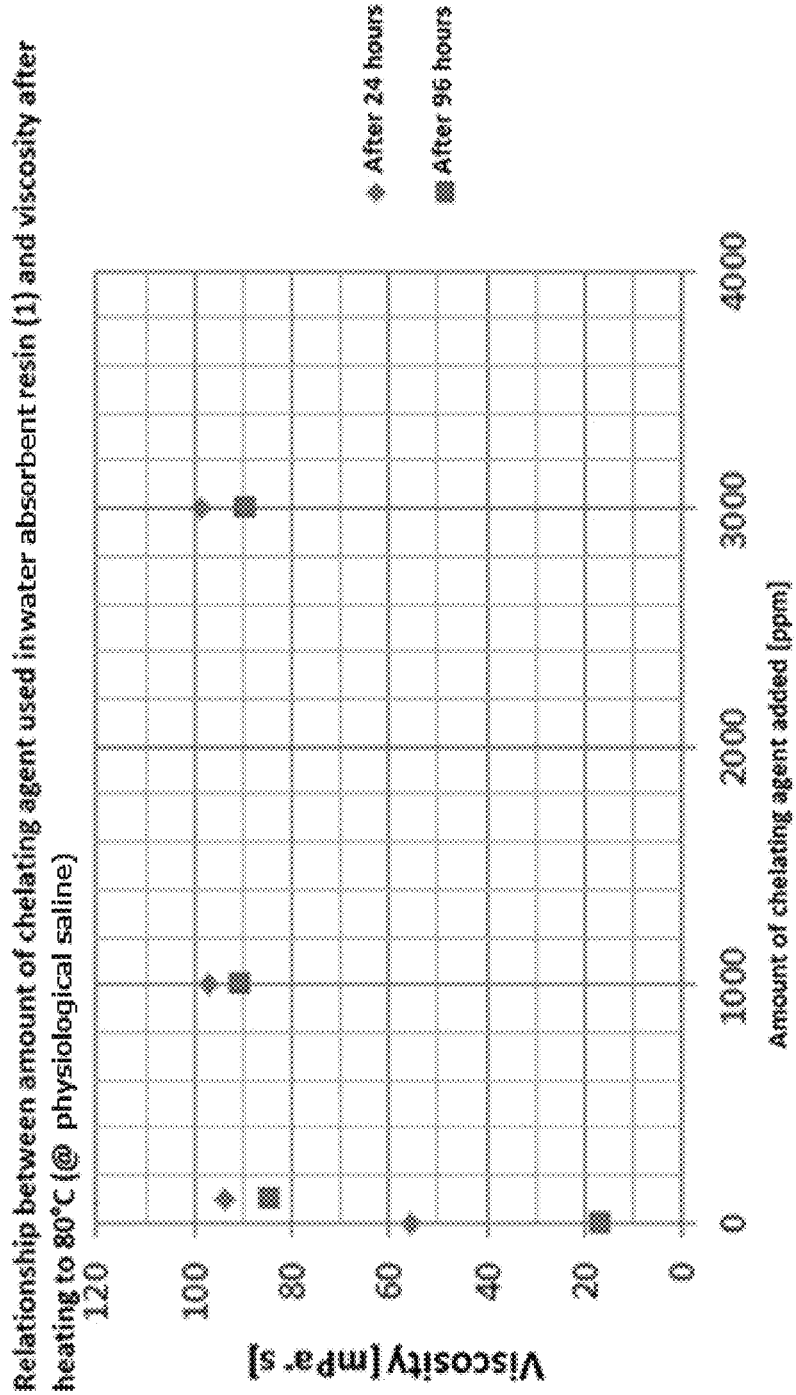

[Figure 11]
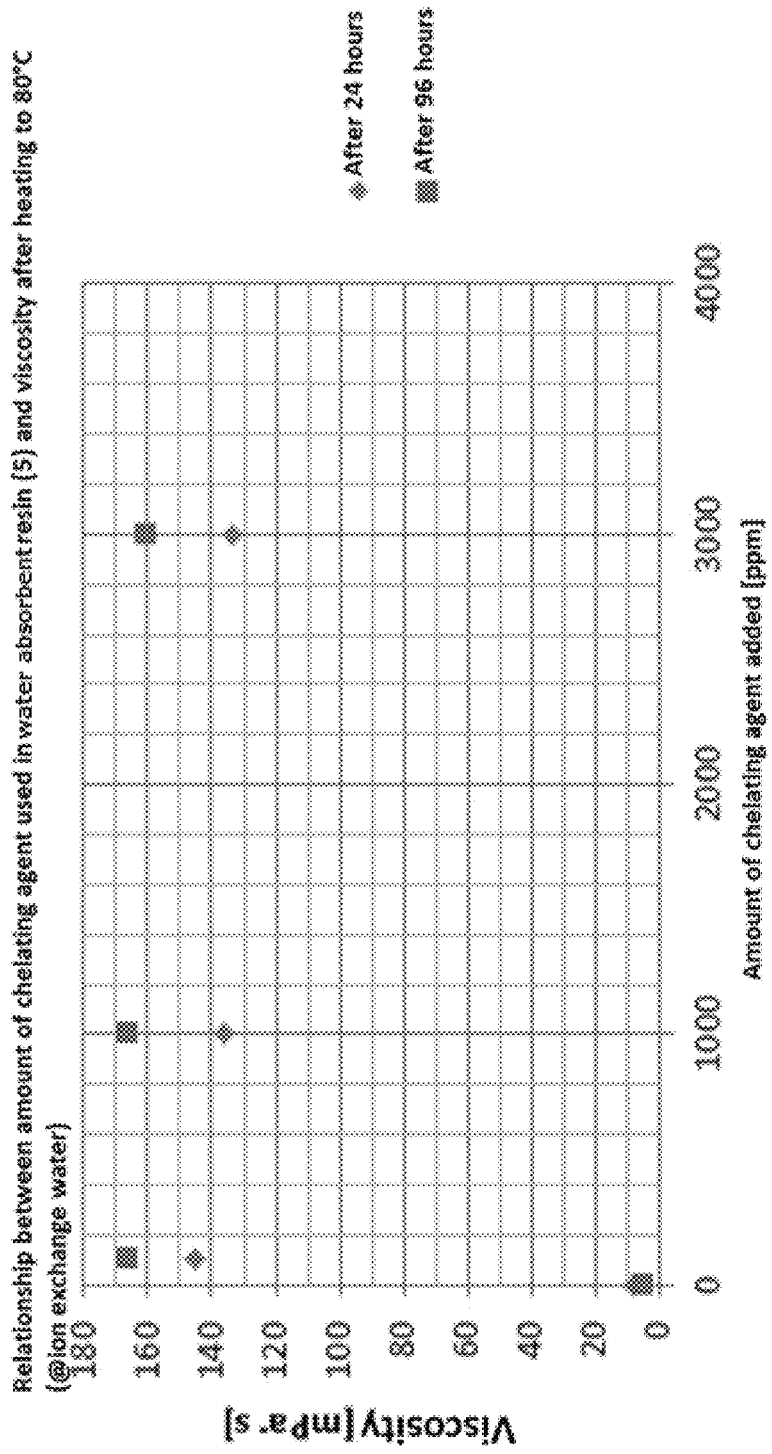

[Figure 12]
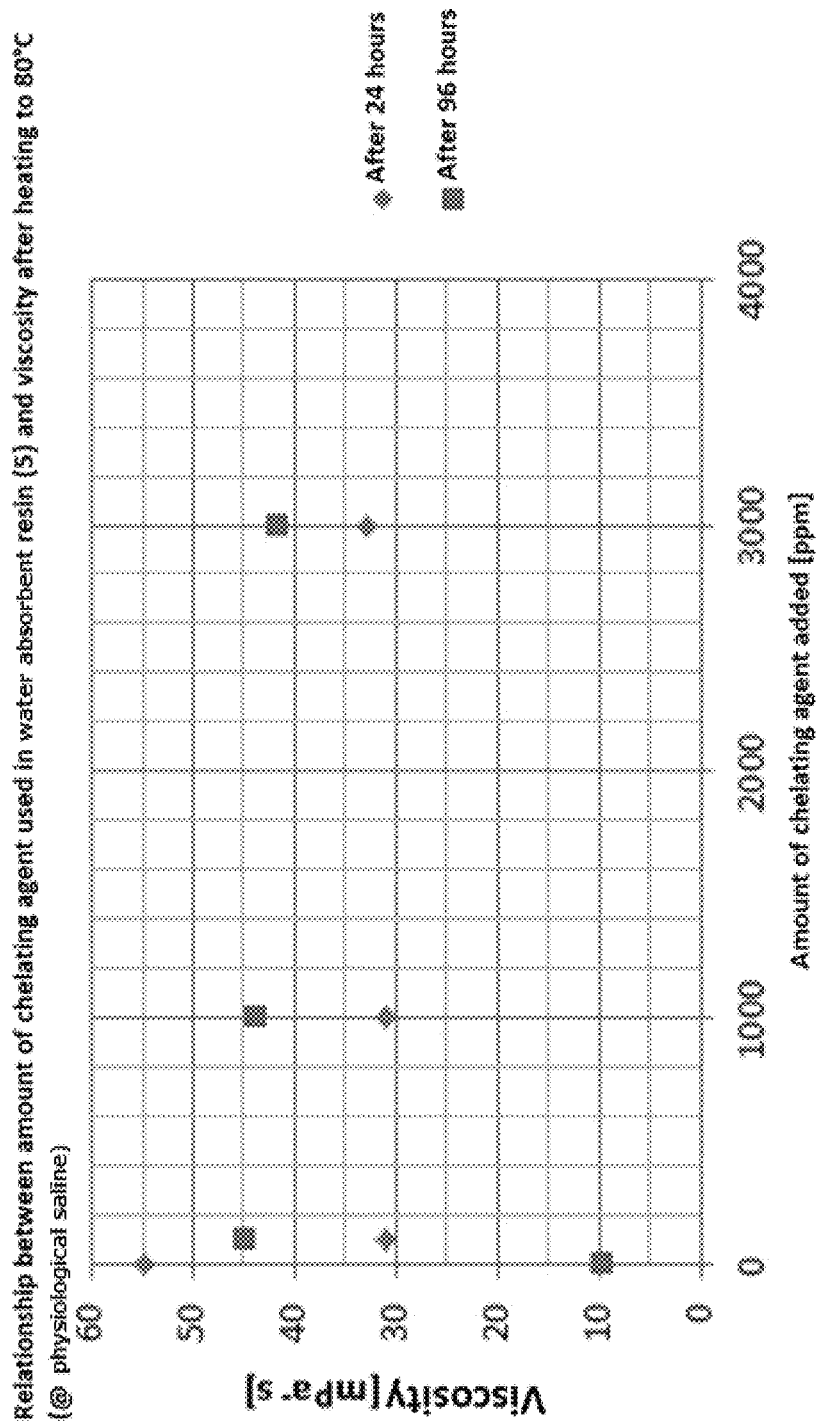

[Figure 13]
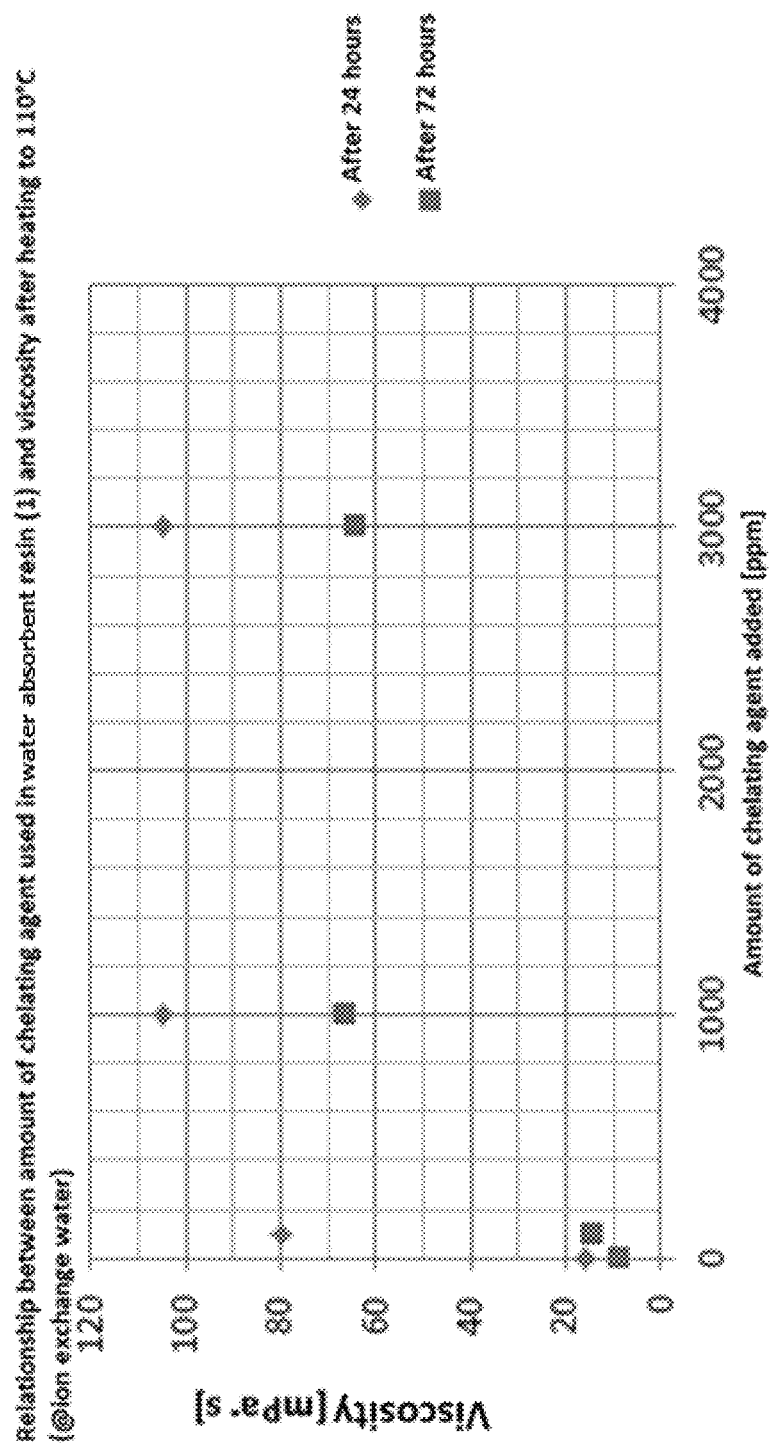

[Figure 14]
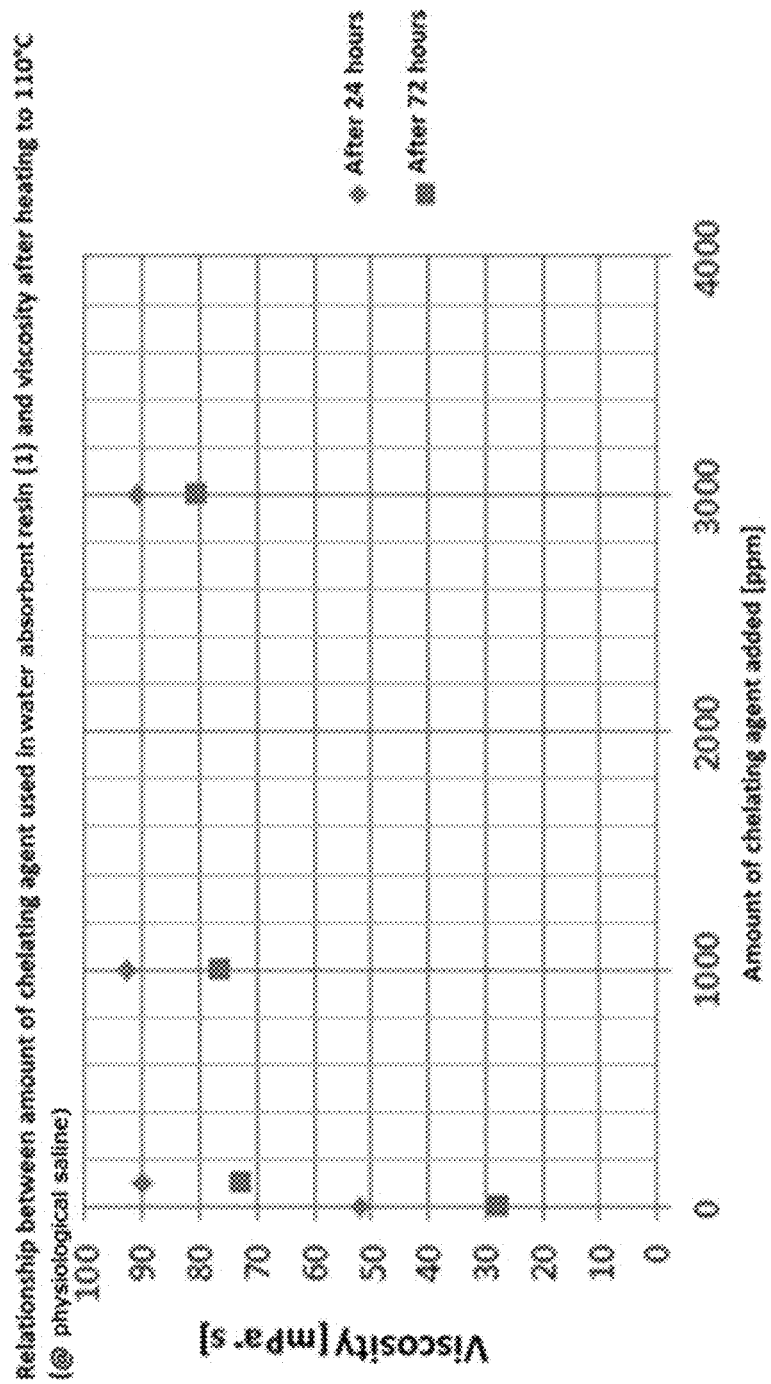

[Figure 15]
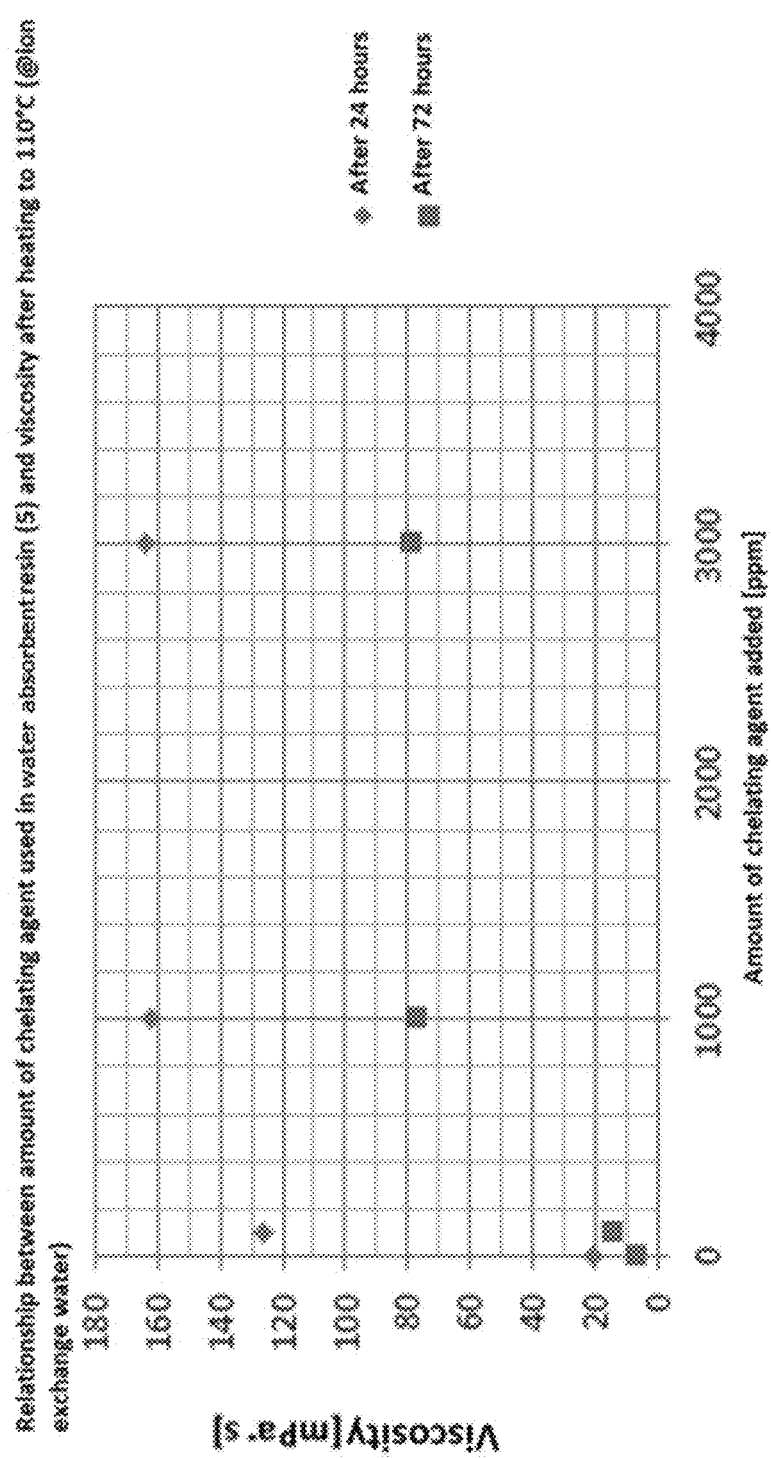

[Figure 16]
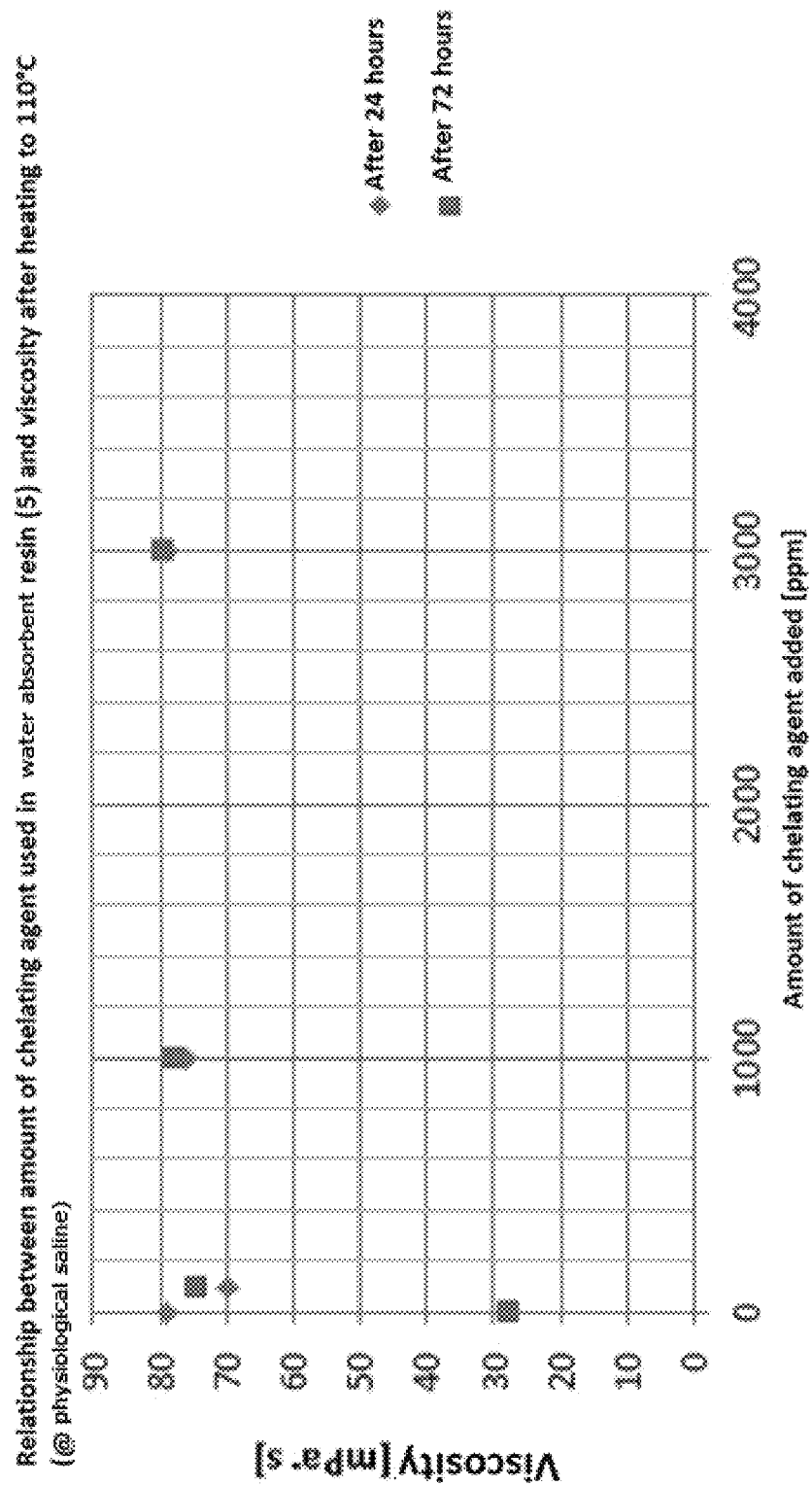

[Figure 17]
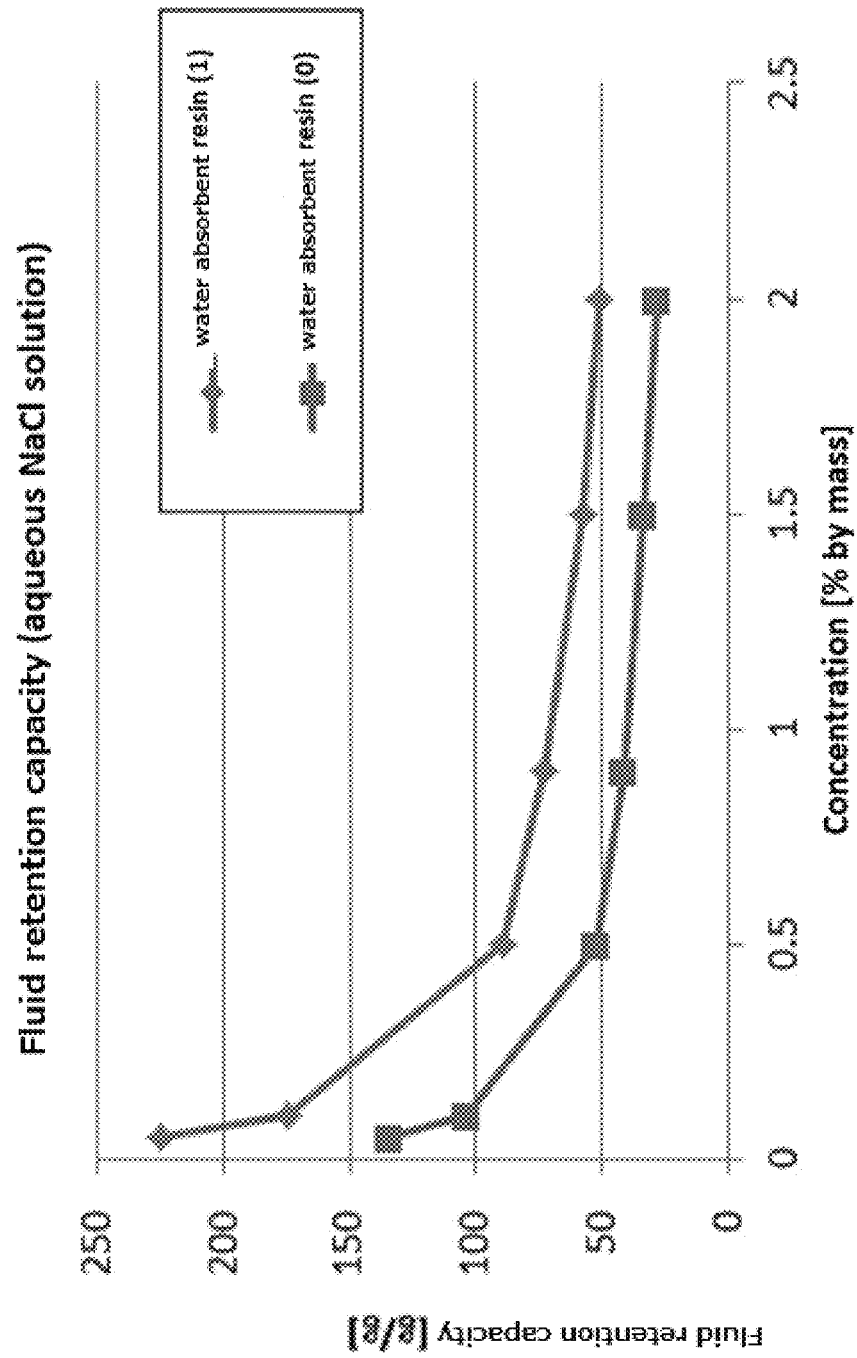

[Figure 18]
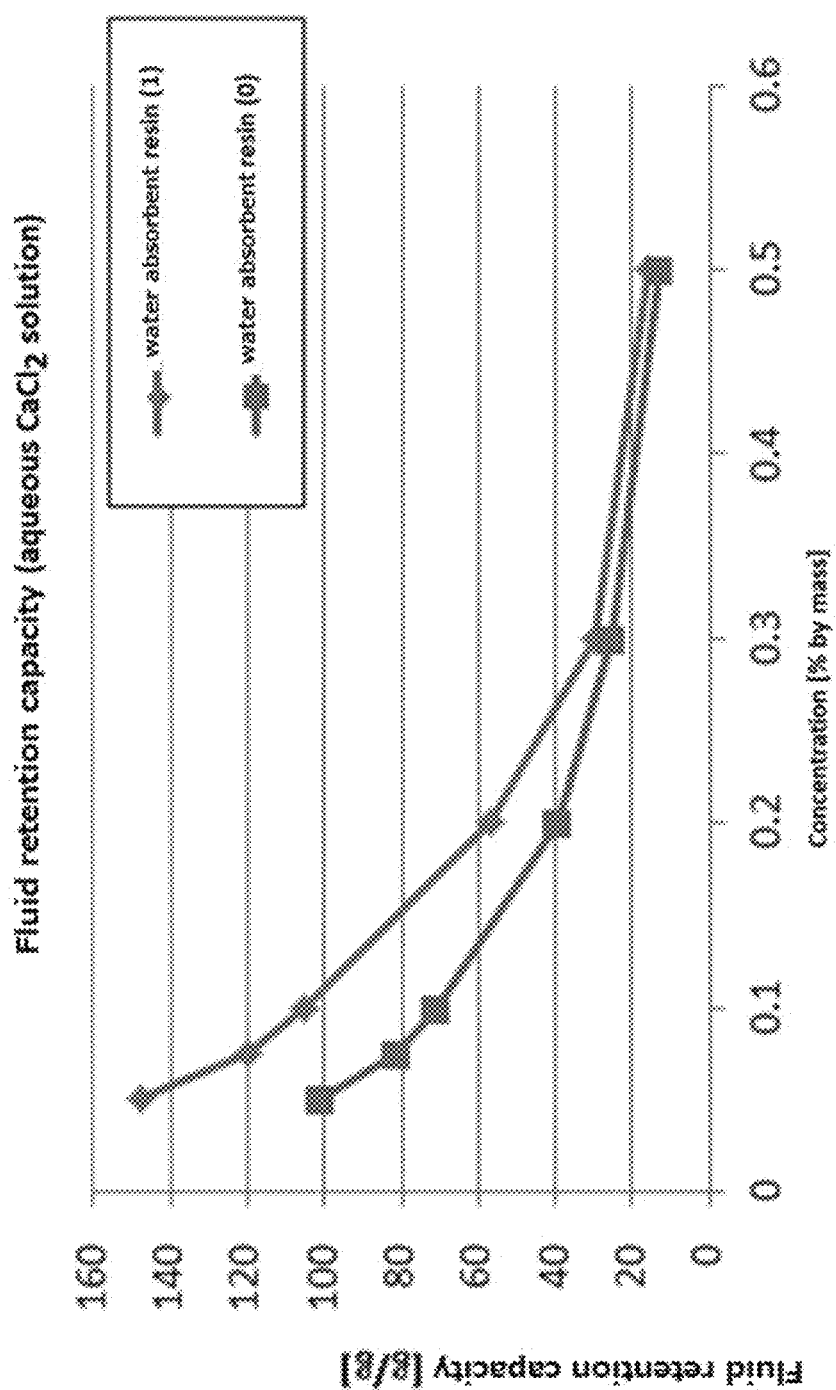

ACRYLIC ACID CROSSLINKED POLYMER AND USE THEREOF

TECHNICAL FIELD

The present invention relates to a novel acrylic acid crosslinked polymer and use thereof in a fluid (fracturing fluid) used in hydraulic fracturing of a stratum. The present invention also relates to a method of determining a water absorbent material that is suitable for a fracturing fluid in a hydraulic fracturing method.

BACKGROUND ART

Hydraulic fracturing of a stratum for mining shale gas is a method that has been practiced for a long time. Natural polysaccharides such as guar gum are often used in fracturing fluid which is used for excavating in hydraulic fracturing in order to improve the viscosity. However, when guar gum is used, it would be necessary to separately add an additional crosslinking agent in order to homogeneously gelate the entire fluid. In most cases, a boric acid-based compound with a relatively high toxicity is used as a crosslinking agent. Meanwhile, use of a water absorbent resin for fracturing fluids has been proposed in recent years.

Patent Literatures 1-4 (US Patent Application Publication No. 2014/0251610, US Patent Application Publication No. 2014/0332213, US Patent Application Publication No. 2014/0332214, and US Patent Application Publication No. 2015/0096751, respectively) disclose the use of a water absorbent resin as a fracturing fluid.

Meanwhile, Patent Literature 5 (International Publication No. WO 2008/126793) discloses a particulate water absorbent agent comprising a polyacrylate-based water-absorbent resin with a high fluid retention capacity as the main component.

CITATION LIST

Patent Literature

[PTL 1] US Patent Application Publication No. 2014/0251610
[PTL 2] US Patent Application Publication No. 2014/0332213
[PTL 3] US Patent Application Publication No. 2014/0332214
[PTL 4] US Patent Application Publication No. 2015/0096751
[PTL 5] International Publication No. WO 2008/126793

SUMMARY OF INVENTION

Solution to Problem

As a result of diligent study, the inventors have discovered a novel acrylic acid crosslinked polymer, which exhibits excellent thickening behavior. While the performance required in applying a water absorbent resin to a gelating system for a fracturing fluid used under pressure was considered the same as the performance required in a water absorbent resin which is used in general hygiene materials, such as a high fluid retention capacity, low soluble content, fluid retention capacity under pressure, high gel strength, and the like, the present invention is based on the surprising discovery that, instead of fluid retention capacity under pressure or the like, a highly soluble content of water absorbent resin exhibits excellent thickening behavior, and coexistence with a chelating agent further improved the stability of viscosity. A sufficient thickening effect, which was not possible with the application of a conventional water absorbent resin, was achieved thereby.

In comparison to conventionally used guar gum-based gelating systems, the effect of reducing required chemical substances and the effect of facilitating breakage and treatment of flowback water can be achieved or enhanced by using the acrylic acid crosslinked polymer of the invention as a fracturing fluid.

The present invention also significantly improves salt tolerance. As water utilized in fracturing fluids, so-called hard water comprising salt, generally lake water, river water, or the like may be used in some cases. Thus, a fracturing fluid with salt tolerance is desirable from the viewpoint of applicability to wells in various locations. Meanwhile, the present invention also meets such a requirement.

By using a technique related to the determination method of the invention, a suitable fracturing fluid can be selected, manufactured, and used considering heat resistance. As a result, a fracturing fluid with improved heat resistance can be provided. A fracturing fluid can be used in a deep underground layer and the underground temperature increases as the depth thereof increases. The geothermal gradient shows the rate of increase in the temperature with respect to the increase in depth in the Earth's interior. The average geothermal gradient up to a depth of over about 10000 m is about 2.5 to 3° C./100 m, the temperature is 65 to 75° C. at a depth of 2000 m, and 95 to 105° C. at a depth of 3000 m. The temperature increases to the same degree up to a depth that is 2000 to 3000 m deeper. The present invention provides a method of determining a water-absorbent material that is suitable as a fracturing fluid in a hydraulic fracturing method and that can be used under such high temperature conditions.

The present invention also provides the following items.
(Item 1A) An acrylic acid crosslinked polymer, wherein an amount of a soluble content is 40 weight % or greater.
(Item 2A) The acrylic acid crosslinked polymer of the preceding item, wherein a weight average molecular weight of the soluble content is one million Dalton or greater.
(Item 3A) The acrylic acid crosslinked polymer according to any one of the preceding items, wherein a fluid retention capacity in physiological saline is 60 g/g or greater, and/or a fluid retention capacity in pure water is 600 g/g or greater.
(Item 4A) The acrylic acid crosslinked polymer according to any one of the preceding items, wherein at least one selected from the amount of soluble content, a weight average molecular weight of the soluble content, and a fluid retention capacity in physiological saline and a fluid retention capacity in pure water is a value related to the acrylic acid crosslinked polymer with a particles size greater than 300 μm and less than 425 μm.
(Item 5A) The acrylic acid crosslinked polymer according to any one of the preceding items, wherein a viscosity upon a dispersion of 0.12 weight % in pure water is 100 mPa·s or greater, and/or the viscosity upon a dispersion of 0.72 weight % in physiological saline is 20 mPa·s or greater.
(Item 6A) The acrylic acid crosslinked polymer according to any one of the preceding items, wherein the polymer is a particle with an average particle diameter (D50) of 10 μm or greater.

(Item 7A) A gelation thickening agent comprising the acrylic acid crosslinked polymer according to any one of the preceding items.

(Item 8A) A water absorbent agent for a fracturing fluid in a hydraulic fracturing method, comprising the acrylic acid crosslinked polymer according to any one of the preceding items.

(Item 9A) The water absorbent agent for a fracturing fluid in a hydraulic fracturing method according to any one of the preceding items, wherein a neutralization rate of the acrylic acid crosslinked polymer is greater than 75 mole %.

(Item 10A) An additive for a water absorbent agent for a fracturing fluid in a hydraulic fracturing method, comprising a chelating agent.

(Item 11A) An additive for a water absorbent agent for a fracturing fluid in a hydraulic fracturing method, comprising a raw material of the acrylic acid crosslinked polymer and a crosslinking agent.

(Item 12A) A kit for a water absorbent agent for a fracturing fluid in a hydraulic fracturing method, comprising a chelating agent and the acrylic acid crosslinked polymer according to any one of the preceding items.

(Item 13A) The additive according to any one of the preceding items or the kit according to any one of the preceding items, wherein the chelating agent is selected from diethylenetriamine pentaacetic acid or a salt thereof.

(Item 14A) The additive according to any one of the preceding items, characterized in that the crosslinking agent is triallyl isocyanurate.

(Item 15A) A method of adjusting the viscosity of a fracturing fluid in a hydraulic fracturing method, comprising the steps:
A) measuring a metal cation type and an amount thereof in water, which is subjected to an adjustment in viscosity;
B) selecting a type and an amount of the acrylic acid crosslinked polymer according to any one of the preceding items so that a viscosity required for fracturing in the hydraulic fracturing method is obtained, based on the metal cation type, and the amount thereof, and pH; and
C) adjusting the viscosity of the fracturing fluid using the selected type and amount of the acrylic acid crosslinked polymer.

(Item 16A)
The method according to any one of the preceding items, wherein the type and/or amount of the polymer is determined based on a soluble content.

(Item 17A) The method according to any one of the preceding items, characterized by further taking into consideration a weight average molecular weight of the soluble content of the polymer.

(Item 18A)
The method according to any one of the preceding items, characterized by further adjusting the viscosity using a chelating agent.

(Item 1)
A method of determining a water absorbent material that is suitable for a fracturing fluid in a hydraulic fracturing method, comprising the steps:
1) measuring, under a normal temperature, a relationship between an amount of a polymer used in the material and a viscosity of the polymer in a fluid medium;
2) determining an amount of the polymer at which the viscosity is at or greater than a predetermined viscosity;
3) adding a variable amount of a chelating agent to the polymer with a certain amount satisfying the condition determined in 2) and measuring a change over time in viscosity in the fluid medium, under a predetermined high temperature condition;
4) determining an amount of the chelating agent when the viscosity become stabilized over time based on the measurement in 3); and
5) employing the certain amount of the polymer and the amount of the chelating agent when the viscosity become stabilized in 4) if the viscosity measured in 3) if the viscosity is a suspension retainable viscosity, but not if the viscosity is not a suspension retainable viscosity.

(Item 2)
The method of item 1, comprising a step of 6) repeating 3) to 5) if the viscosity measured in 3) is not a suspension retainable viscosity in 5).

(Item 3)
The method according to any one of items 1 to 2, comprising a step of measuring or selecting a fluid retention capacity of the polymer.

(Item 4)
The method according to any one of items 1 to 3, wherein the fluid medium is water used in the hydraulic fracturing method or water having hardness that is equivalent to that of said water.

(Item 5)
The method according to any one of items 1 to 4, further comprising a step of performing a precipitation test using a proppant particle.

(Item 6)
The method according to any one of items 1 to 5, wherein the polymer is a water absorbent resin.

(Item 7)
The method of item 6, wherein the water absorbent resin is an acrylic acid crosslinked polymer.

(Item 8)
The method of item 7, wherein the acrylic acid crosslinked polymer is a crosslinked polymer comprising polyacrylic acid, sodium polyacrylate, or polyacrylamide and/or a mixture thereof.

(Item 9)
A method of manufacturing a fracturing fluid for a hydraulic fracturing method, comprising the steps of 1) to 5) and/or 6) according to any one of items 1 to 8, and a step of 7) manufacturing a fracturing fluid using the certain amount of the polymer and the amount of the chelating agent.

(Item 10)
A hydraulic fracturing method, comprising the steps of 1) to 5) and/or 6) according to any one of items 1 to 9 and/or the step of 7) of item 9, and a step of performing hydraulic fracturing using the certain amount of the polymer and the amount of chelating agent or using the fracturing fluid.

(Item 11)
An acrylic acid crosslinked polymer, wherein an amount of a soluble content is 40 weight % or greater.

(Item 12)
The acrylic acid crosslinked polymer of item 11, wherein a weight average molecular weight of the soluble content is one million Dalton or greater.

(Item 13)
The acrylic acid crosslinked polymer of item 11 or 12, wherein a fluid retention capacity in physiological saline is 60 g/g or greater and/or a fluid retention capacity in ion exchange water is 600 g/g or greater.

(Item 14)
The acrylic acid crosslinked polymer according to any one of items 11 to 13, wherein at least one selected from the amount of soluble content, a weight average molecular weight of the soluble content, a fluid retention capacity in physiological saline and a fluid retention capacity in ion exchange water is a value related to the acrylic acid crosslinked polymer with a particles size greater than 300 µm and less than 425 µm.

(Item 15)
The acrylic acid crosslinked polymer according to any one of items 11 to 14, wherein a viscosity upon a 0.12 weight % dispersion in ion exchange water is 100 mPa·s or greater and/or a viscosity upon a 0.72 weight % dispersion in physiological saline is 20 mPa·s or greater.

(Item 16)
The acrylic acid crosslinked polymer according to any one of items 11 to 15, wherein the polymer is a particle with an average particle diameter (D50) of 10 µm or greater.

(Item 17)
A gelation thickening agent comprising the acrylic acid crosslinked polymer according to any one of items 11 to 16.

(Item 18)
A water absorbent agent for a fracturing fluid in a hydraulic fracturing method, comprising the acrylic acid crosslinked polymer according to any one of items 11 to 16.

(Item 19)
The water absorbent agent for a fracturing fluid in a hydraulic fracturing method of item 18, wherein a neutralization rate of the acrylic acid crosslinked polymer is greater than 75 mole %.

(Item 20)
The water absorbent agent of item 18 or 19, comprising a chelating agent at 0.01 weight % or greater.

(Item 21)
The water absorbent agent according to any one of items 18 to 20, comprising a chelating agent at 0.1 weight % or greater.

(Item 22)
An additive for a water absorbent agent for a fracturing fluid in a hydraulic fracturing method, comprising a chelating agent.

(Item 23)
An additive for a water absorbent agent for a fracturing fluid in a hydraulic fracturing method, comprising a raw material of the acrylic acid crosslinked polymer according to any one of items 11 to 16 and a crosslinking agent.

(Item 24)
A kit for a water absorbent agent for a fracturing fluid in a hydraulic fracturing method, comprising an acrylic acid crosslinked polymer comprising a chelating agent and/or a chelating agent and an acrylic acid crosslinked polymer.

(Item 25)
The kit for a water absorbent agent for a fracturing fluid in a hydraulic fracturing method of item 24, wherein the acrylic acid crosslinked polymer comprises the acrylic acid crosslinked polymer according to any one of items 11 to 16.

(Item 26)
The additive of item 22 or the kit of item 24 or 25, wherein the chelating agent is selected from diethylenetriamine pentaacetic acid or a salt thereof.

(Item 27)
The kit according to any one of items 24 to 26, comprising the chelating agent at 0.01 weight % or greater.

(Item 28)
The kit according to any one of items 24 to 26, comprising the chelating agent at 0.1 weight % or greater.

(Item 29)
The additive of item 23, characterized in that the crosslinking agent is triallyl isocyanurate.

(Item 30)
A hydraulic fracturing method comprising a step of performing hydraulic fracturing using a water absorbent agent for a fracturing fluid, wherein the water absorbent agent for a fracturing fluid comprise the acrylic acid crosslinked polymer according to any one of items 11 to 16.

(Item 31)
The hydraulic fracturing method of item 30, wherein a neutralization rate of the acrylic acid crosslinked polymer is greater than 75 mole %.

(Item 32)
The hydraulic fracturing method according to any one of items 30 to 31, using a chelating agent at 0.01 weight % or greater.

(Item 33)
The hydraulic fracturing method according to any one of items 30 to 32, using a chelating agent at 0.1 weight % or greater.

(Item 34)
A hydraulic fracturing method comprising a step of performing hydraulic fracturing using an additive for a water absorbent agent for a fracturing fluid, wherein the additive for the water absorbent agent comprise a chelating agent.

(Item 35)
A hydraulic fracturing method comprising a step of performing hydraulic fracturing using an additive for a water absorbent agent for a fracturing fluid, wherein the additive for the water absorbent agent comprise a raw material of the acrylic acid crosslinked polymer according to any one of items 11 to 16 and a crosslinking agent.

(Item 36)
A hydraulic fracturing method comprising a step of performing hydraulic fracturing using a kit for a water absorbent agent for a fracturing fluid, wherein the kit for the water absorbent agent comprise an acrylic acid crosslinked polymer comprising a chelating agent and/or a chelating agent and an acrylic acid crosslinked polymer.

(Item 37)
The hydraulic fracturing method of item 36, wherein the acrylic acid crosslinked polymer comprises the acrylic acid crosslinked polymer according to any one of items 11 to 16.

(Item 38)
The hydraulic fracturing method of item 34, 36, or 37, wherein the chelating agent is selected from diethylenetriamine pentaacetic acid or a salt thereof.

(Item 39)
The hydraulic fracturing method according to any one of items 36 to 38, using the chelating agent at 0.01 weight % or greater.

(Item 40)
The hydraulic fracturing method according to any one of items 36 to 39, using the chelating agent at 0.1 weight % or greater.

(Item 41)
The hydraulic fracturing method of item 35, characterized in that the crosslinking agent is triallyl isocyanurate.

(Item 42)
A method of adjusting viscosity of a fracturing fluid in a hydraulic fracturing method, comprising the steps:
A) measuring a metal cation type and an amount thereof in water, which is subjected to viscosity adjustment;
B) selecting a type and amount of the acrylic acid crosslinked polymer according to any one of items 11 to 16 so that a viscosity required for fracturing in the hydraulic fracturing method is obtained, based on the metal cation type, and the amount thereof, and pH; and C) adjusting the viscosity of the fracturing fluid using the selected type and amount of the acrylic acid crosslinked polymer.
(Item 43)
The method item 42, wherein the type and/or amount of the polymer is determined based on a soluble content.
(Item 44)
The method item 42 or 43, characterized by further taking into consideration a weight average molecular weight of the soluble content of the polymer.
(Item 45)
The method according to any one of items 42 to 44, characterized by further adjusting the viscosity using a chelating agent.

In the present invention, one or more of the features described above are intended to be provided not only as the explicitly described combinations, but also as other combinations thereof. The additional embodiments and advantages of the present invention are recognized by those skilled in the art by reading the following detailed description, as needed.

Advantageous Effects of the Invention

The crosslinked polymer of the invention can be advantageously used in fracturing fluids and the like due to a greater thickening effect on water with a wider range of hardness than conventional known polymers used in water absorbent resins. Moreover, the crosslinked polymer of the invention can reduce the burden on the environment because the type and amount of additives in a fracturing fluid composition can be reduced.

BRIEF DESCRIPTION OF DRAWINGS

FIG. 1 is a graph of measurement time vs. viscosity for the acrylic acid crosslinked polymer in physiological saline (amount added: 0.72 wt. %) in each Test Example.

FIG. 2 is a graph of measurement time vs. viscosity for the acrylic acid crosslinked polymer in ion exchange water (amount added: 0.12 wt. %) in each Test Example.

FIG. 3 shows the relationship between the amount of water absorbent resin (0) used and viscosity (viscosity after 30 minutes) in ion exchange water.

FIG. 4 shows the relationship between the amount of water absorbent resin (0) used and viscosity (viscosity after 30 minutes) in physiological saline.

FIG. 5 shows the relationship between the amount of water absorbent resin (1) used and viscosity (viscosity after 30 minutes) in ion exchange water.

FIG. 6 shows the relationship between the amount of water absorbent resin (1) used and viscosity (viscosity after 30 minutes) in physiological saline.

FIG. 7 shows a sand (sea sand) dispersion and precipitation test of the water absorbent resin (1) and the non-crosslinked polymer (6).

FIG. 8 shows the sand (sea sand) dispersion and precipitation test of water absorbent resin (1) at a viscosity of 139 mPa·s, 81 mPa·s, and 59 mPa·s.

FIG. 9 shows the relationship between the amount of chelating agent of water absorbent resin (1) and viscosity (2 minute stable value) after a 80° C. heat resistance test in ion exchange water.

FIG. 10 shows the relationship between the amount of chelating agent of water absorbent resin (1) and viscosity (2 minute stable value) after a 80° C. heat resistance test in physiological saline.

FIG. 11 shows the relationship between the amount of chelating agent of water absorbent resin (5) and viscosity (2 minute stable value) after a 80° C. heat resistance test in ion exchange water.

FIG. 12 shows the relationship between the amount of chelating agent of water absorbent resin (5) and viscosity (2 minute stable value) after a 80° C. heat resistance test in physiological saline.

FIG. 13 shows the relationship between the amount of chelating agent of water absorbent resin (1) and viscosity (2 minute stable value) after a 110° C. heat resistance test in ion exchange water.

FIG. 14 shows the relationship between the amount of chelating agent of water absorbent resin (1) and viscosity (2 minute stable value) after a 110° C. heat resistance test in physiological saline.

FIG. 15 shows the relationship between the amount of chelating agent of water absorbent resin (5) and viscosity (2 minute stable value) after a 110° C. heat resistance test in ion exchange water.

FIG. 16 shows the relationship between the amount of chelating agent of water absorbent resin (5) and viscosity (2 minute stable value) after a 110° C. heat resistance test in physiological saline.

FIG. 17 shows the relationship between the fluid retention capacity and the concentration when an absorbed liquid is an aqueous NaCl solution.

FIG. 18 shows the relationship between the fluid retention capacity and the concentration when the absorbed liquid is an aqueous $CaCl_2$ solution.

DESCRIPTION OF EMBODIMENTS

The present invention is explained hereinafter while disclosing the best mode of the invention. Throughout the entire specification, a singular expression should be understood as encompassing the concept thereof in the plural form, unless specifically noted otherwise. Thus, singular articles (e.g., "a", "an", "the", and the like, in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The terms used herein are explained hereinafter.

[1] Definitions of Terms (1-1) "Acrylic Acid Crosslinked Polymer"

"Acrylic acid crosslinked polymer" in the present invention refers to a polymer comprising a repeating unit derived from an acrylic acid (salt) and a structural unit derived from a crosslinking agent (hereinafter, also referred to as "internal crosslinking agent") as the main component. An acrylic acid crosslinked polymer can be used as a water absorbent resin.

(1-2) "Water Absorbent Resin"

"Water absorbent resin" in the present invention refers to a water-swellable water-insoluble polymer gelling agent satisfying the following properties, i.e., a polymer gelling agent satisfying the following physical properties: CRC as specified in ERT441.2-02 of 60 g/g or greater as "water swellable"; and Ext as specified in ERT470.2-02 of 40 weight % or greater as "water-insoluble". The polymer of the invention can be used as a water absorbent resin. A water absorbent resin can be used as a water-absorbent material.

The above-described water absorbent resin can be appropriately designed depending on its use. The water absorbent resin is not limited to a form in which the entire amount (100 weight %) is a polymer. The above-described water absorbent resin may be a water absorbent resin composition comprising an additive or the like, to the extent that the above-described physical properties (CRC and Ext) are satisfied.

Moreover, the water absorbent resin in the present invention may refer to not only final products, but also intermediates in the manufacturing process of a water absorbent resin (for example, crosslinked hydrogel polymer after polymerization, a dried polymer after drying, and the like). These all, in combination with the above-described water absorbent resin compositions, are named a "water absorbent resin" comprehensively. Examples of shapes of a water absorbent resin include sheet form, fiber form, film form, particle form, and gel form and the like.

(1-2-1) "Water Absorbent Material"

The water absorbent material in the present invention refers to any water absorbent material that is suitable for use in a fracturing fluid in a hydraulic fracturing method, comprising a polymer and a chelating agent. Depending on the objective of the present invention, a substance called a "thickening agent" can also be used as a "polymer" in the art. Examples of water absorbent materials include water absorbent resins, water absorbent crosslinked polymers, and the like. Specific embodiments of the water absorbent material that can be used in the present invention include crosslinked polymers of copolymers and homopolymers such as polyacrylic acid, sodium polyacrylate, polyacrylamide and the like, and mixtures thereof.

(1-2-2) "Water Absorbent Agent"

Water absorbent agents in the present invention refer to water-swellable water-insoluble polymer gelling agents used in fracturing fluids in hydraulic fracturing methods, which satisfy the following physical properties: CRC as specified in ERT441.2-02 of 60 g/g or greater as "water swellable"; and Ext as specified in ERT470.2-02 of 40 weight % or greater as "water-insoluble".

(1-3) Details of Polymers

Acrylic acid and/or a salt thereof (hereinafter, referred to as "acrylic acid (salt)") is used as a monomer as a raw material of the acrylic acid crosslinked polymer of the invention from the viewpoint of physical properties and productivity of a resulting acrylic acid crosslinked polymer. The above-described "acrylic acid" may be a known acrylic acid, preferably comprising a methoxyphenol and more preferably p-methoxyphenol as a polymerization inhibitor at preferably 200 ppm or less, more preferably at 10 to 160 p$\mu$m, and still more preferably at 20 to 100 ppm from the viewpoint of polymerizability of the acrylic acid or hue of a water absorbent resin. The compound described in US Patent Application No. 2008/0161512 is also applied for impurities in acrylic acids.

In addition, the above-described "acrylic acid salt" is a salt resulting from neutralization of the above-described acrylic acid with a basic composition disclosed below. Such acrylic acid salts may be a commercially available acrylic acid salt (e.g., sodium acrylate) or a salt obtained by neutralization in a production plant of a water absorbent resin.

(Basic Composition)

"Basic composition" refers to a composition including a basic compound, and for example, commercially available aqueous sodium hydroxide solutions and the like fall thereunder.

Specific examples of the above-described basic compounds include carbonate salts and bicarbonate salts of alkali metals, hydroxides of alkali metals, ammonia, organic amines, and the like. Among these, from the viewpoint of physical properties of the resulting water absorbent resin, it is desired to be strongly basic. That is, alkali metal hydroxides, such as sodium hydroxide, potassium hydroxide, lithium hydroxide, and the like are preferable, and sodium hydroxide is more preferable.

(Neutralization)

As neutralization, either neutralization of acrylic acid (before polymerization) or neutralization of crosslinked hydrogel polymer obtained by crosslink polymerization of acrylic acid (after polymerization) (hereinafter, referred to as "subsequent neutralization") can be selected or they can be used in combination. In addition, these neutralizations may be a continuous or batch type, and are not particularly limited. However, the continuous type is preferable from the viewpoint of production efficiency and the like.

It should be noted that regarding conditions including apparatus to perform neutralization, neutralization temperature, residence time, and the like, conditions described in International Publication No. WO 2009/123197 and US Patent Application Publication No. 2008/0194863 are also applied to the present invention.

A neutralization rate, with respect to an acid group of a monomer, is preferably 10 to 100 mole %, more preferably 40 to 98 mole %, still more preferably 50 to 95 mole %, and especially preferably 60 to 90 mole %. When the neutralization rate is less than 10 mole %, the fluid retention capacity may decrease significantly. On the other hand, a high neutralization rate and high pH, as described in JP 4209173, are preferable, as the durability of water absorbent resin is enhanced. Meanwhile, mole % greater than 100 may result in hydrolysis when the internal crosslinking agent disclosed below has an ester structure.

Regarding the above-described neutralization rate, the same applies in the case of the subsequent neutralization. Regarding the neutralization rate of a water absorbent resin as a final product, the above-described neutralization rate is also applied. It should be noted that a neutralization rate of 75 mol % means a mixture of 25 mol % of acrylic acid and 75 mol % of an acrylic acid salt. Moreover, the mixture may be referred to as the partially neutralized acrylic acid.

(Other Monomers)

"Other monomers" refers to monomers other than the above-described acrylic acid (salt), and can be used in combination with acrylic acid (salt) to produce a water absorbent material such as a water absorbent resin and the like.

Examples of the above-described "other monomers" include water-soluble or hydrophobic unsaturated monomers. Specifically, compounds described in US Patent Application No. 2005/0215734 (except acrylic acids) are also applied.

(Internal Crosslinking Agent)

As an internal crosslinking agent to be used, compounds described in U.S. Pat. No. 6,241,928 are also applicable to the present invention. From these one type or two types or more of compounds are selected in view of the reactivity.

Examples of such polymerizable crosslinking agents include N,N'-methylenebisacrylamide, (poly)ethylene glycol di(meth)acrylate, (polyoxyethylene)trimethylol propane tri(meth)acrylate, triallyl isocyanurate, triallyl phosphate, triallylamine, poly(meth)allyloxy alkane and other compounds with at least two polymerizable double bonds in the molecule. Further, examples of the above-described reactive crosslinking agents include covalent bond crosslinking agents such as polyglycidyl ether such as ethylene glycol diglycidyl ether and the like, polyhydric alcohol and the like such as propanediol, glycerol, sorbitol and the like; ionic bond crosslinking agents such as multivalent metal compounds and the like including aluminum salt and the like. Among them, from the viewpoint of fluid retention performance, crosslinking agents that are polymerizable with acrylic acid are more preferable, and acrylate-based, allyl based, and acrylamide based polymerizable crosslinking agents are especially preferable. One type of internal crosslinking agent may be used alone or two or more types may be used in combination. When the above-described polymerizable crosslinking agent and covalent bond crosslinking agent are used in combination, the mix ratio thereof is preferably 10:1 to 1:10.

The amount of above-described internal crosslinking agent used varies depending on the concentration of an aqueous monomer solution, but is preferably 0.0001 to 0.1 mole %, more preferably 0.0005 to 0.05 mole %, and still more preferably 0.001 to 0.03 with respect to the entire monomer. A desirable water absorbent resin can be obtained with said amount within the above-described range. When said amount is too low, gel strength decreases so that swellable gel can no longer maintain a particulate form. When said amount is too high, the fluid retention capacity tends to decrease, which is not preferable.

A method of performing a crosslinking reaction simultaneously with polymerization by previously adding a predetermined amount of an internal crosslinking agent to an aqueous monomer solution is preferably applied. On the other hand, other than the technique, the following methods can be adopted: a method of after crosslinking by adding an internal crosslinking agent during or after polymerization; a method of radically crosslinking using a radical polymerization initiator; a method of radiation-induced crosslinking using active energy ray such as electron ray, ultraviolet ray, and the like; and the like. Further, these methods can be used in combination.

(Other Substances Added to an Aqueous Monomer Solution)

From the viewpoint of improving the physical properties of a resulting water absorbent material such as a water absorbent resin and the like, the following substances can also be added in preparing an aqueous monomer solution.

Specifically, a hydrophilic polymer such as starch, starch derivatives, cellulose, cellulose derivatives, polyvinyl alcohol, polyacrylic acid (salt), crosslinked polyacrylic acid (salt) and the like, can be added in preferably 50 weight % or less, more preferably 20 weight % or less, further preferably 10 weight % or less, and particularly preferably 5 weight % or less (the lower limit is 0 weight %), as well, a carbonate salt, an azo compound, a foaming agent such as air bubble and the like, a surfactant, a chelating agent, a chain-transfer agent and the like can be added in preferably 5 weight % or less, more preferably 1 weight % or less, further preferably 0.5 weight % or less (the lower limit is 0 weight %).

In addition, the above-described substances may be added to an aqueous monomer solution, or added in the middle of polymerization, and these addition procedures can be used in combination. It should be noted that when a water-soluble resin or a water absorbent resin is used as a hydrophilic polymer, a graft polymer or a water absorbent resin composition (e.g., starch-acrylic acid polymer, PVA-acrylic acid polymer, and the like) is obtained. These polymers and water absorbent resin compositions also fall within the scope of the present invention.

(Concentration of Monomer Component)

In the present step, each substance described above is added in preparing an aqueous monomer solution. The concentration of the monomer component in the aqueous monomer solution is, but not particularly limited to, preferably 10 to 80 weight %, more preferably 20 to 75 weight %, further preferably 30 to 70 weight %, and especially preferably 40 to 60 weight % from the viewpoints of physical properties of the water absorbent resin.

In addition, when aqueous solution polymerization or reverse phase suspension polymerization is adopted, a solvent other than water can be used in combination as necessary. In this case, the type of the solvent is not particularly limited.

It should be noted that the above-described "the concentration of a monomer component" is a value obtained by the following formula (1), wherein the weight of an aqueous monomer solution does not include the weight of a graft component, a water absorbent resin and hydrophobic solvent used on a reverse-phase suspension polymerization.

(The concentration of the monomer component (weight %))=(The weight of the monomer component)/(The weight of the aqueous monomer solution)×100 [Formula 1]

(Chelating Agent)

As a chelating agent, the specific compound and amount used that are disclosed in "[2] Chelating agent" in International Publication No. WO 2011/040530 are applicable to the present invention. Diethylenetriamine pentaacetic acid, triethylenetetraamine hexaacetic acid, and salts thereof, in particular, are suitably used.

In one aspect, a chelating agent can be used to stabilize a change in viscosity over time of a water absorbent material in a fluid medium at high temperatures. Chelating agents may be added to a water absorbent material or may be contained in an absorbed liquid.

(Inorganic Reducing Agent)

From the viewpoints of the color tone (prevention of coloring), prevention of deterioration, decreased residual monomers and the like of the resulting water absorbent resin, it is preferable to add an inorganic reducing agent. As the above-described inorganic reducing agent, specifically, compounds and the amounts used thereof disclosed in "[3] Inorganic reducing agent" of International Publication No. 2011/040530 are applied to the present invention.

(α-Hydroxycarboxylic Acid Compound)

From the viewpoints of the color tone (prevention of coloring) of the resulting water absorbent resin and the like, it is preferable to add α-hydroxycarboxylic acid. It should be noted that "α-hydroxycarboxylic acid compound" refers to a carboxylic acid or a salt thereof that has a hydroxyl group in its molecule at α-position.

As the above-described α-hydroxycarboxylic acid compound, specifically, compounds and the amount used thereof disclosed in "[6] α-hydroxycarboxylic acid compound" of International Publication No. 2011/040530 are applied to the present invention.

(1-4) "EDANA" and "ERT"

"EDANA" is an abbreviation of the 'European Disposables and Nonwovens Association', and "ERT" is an abbreviation of a method for measuring a water absorbent resin which is European standard (approximately world standard)

(EDANA Recommended Test Methods). Since a water absorbent resin is widely used for hygienic material application, also in the present invention, physical properties of a water absorbent material such as a water absorbent resin and the like are measured in conformity with the original document of ERT (revised in 2002/publicly-known reference) unless indicated otherwise.

(1-4-1) "CRC" (ERT441.2-0, 2)

"CRC" is an abbreviation of 'Centrifuge Retention Capacity', and means fluid retention capacity without pressure of a water absorbent material such as a water absorbent resin and the like (hereinafter referred to as "fluid retention capacity" in some cases).

(1-4-2) "AAP" (ERT442.2-02)

"AAP" is an abbreviation of Absorption Against Pressure, and means fluid retention capacity under pressure of a water absorbent material such as a water absorbent resin and the like.

Specifically, "AAP" means fluid retention capacity (unit; g/g) obtained after 0.9 g of a water absorbent material such as a water absorbent resin and the like is swollen in 0.9 wt % of aqueous sodium chloride solution in a largely excessive amount under a load of 2.06 kPa (21 g/cm$^2$, 0.3 psi) for 1 hour. In some measurements, the pressure condition is changed to 4.83 kPa (49 g/cm$^2$, 0.7 psi)

ERT442.2-02 also recites "Absorption Under Pressure", which substantially means the same.

(1-4-3) "PSD" (ERT420.2-02)

"PSD" is an abbreviation of Particle Size Distribution, and means the particle size distribution of a water absorbent material such as a water absorbent resin and the like measured by sieve classification.

It should be noted that a weight average particle diameter (D50) and the logarithmic standard deviation (sigma zeta ($\sigma\zeta$)) of particle size distribution are measured by the similar method to "(3) Mass-Average Particle Diameter (D50) and Logarithmic Standard Deviation (sigma zeta ($\sigma\zeta$)) of Particle Diameter Distribution" described in U.S. Pat. No. 7,638,570.

(1-4-4) "Ext" (ERT470.2-02)

"Ext" is an abbreviation for Extractables, and means a water soluble content (amount of water soluble component) of a water absorbent material such as a water absorbent resin and the like.

Specifically, "Ext" is the amount of dissolved polymer (unit; weight %) after 1.0 g of water absorbent material such as a water absorbent resin and the like is added to 200 ml of 0.9 weight % of aqueous sodium chloride solution and the resulting mixture is stirred for 16 hours at 500 rμm. The amount of dissolved polymer is measured by pH titration.

(1-5) Fluid Retention Capacity

The fluid retention capacity as used herein is a fluid retention capacity (unit: g/g) obtained after a water absorbent resin is immersed in a significantly excessive amount of ion exchange water or an aqueous solution comprising a predetermined amount of salt for 30 minutes and the resin is allowed to freely swell, and then water is drained with a centrifuge (250 G).

The specific measurement procedure is in accordance with the fluid retention capacity measurement procedure in the Test Examples. It should be noted that CRC corresponds to a case where aqueous 0.9 weight % sodium chloride solution is used as the aqueous solution comprising a predetermined amount of salt.

(1-6) Others

As used herein, "X to Y" indicating a range means "X or more and Y or less". In addition, unless particularly remarked, "t (ton)" as a unit of weight, means "Metric ton" and "ppm" means "ppm by weight" or "ppm by mass". Further, "weight" and "mass", "part(s) by weight" and "part(s) by mass", and "weight %" and "mass %" are each handled as synonym. Moreover, " . . . acid (salt)" means " . . . acid and/or a salt thereof", and "(meth)acryl" means "acryl and/or methacryl", respectively.

Particles with a particle size of "Pass A μm/On B μm" refer to particles that pass through a sieve with an mesh size of A μm, but not a sieve with an mesh size of B μm when a sieve is used having an mesh size with the relationship of A μm>B μm.

In addition, for convenience, "liter" may be described as "l" or "L" and "weight %" may be described as "wt %". Further, in measuring a trace component, being not more than a limit of detection is described as N.D. (Not Detected) (the same applies in [Text Example]).

[2] Method of Manufacturing an Acrylic Acid Crosslinked Polymer

Hereinafter, manufacturing steps (2-1) to (2-9) of the water absorbent resin are shown, that is applicable to an example in the present invention. The water absorbent materials targeted by the determination method of the present invention include, but are not limited to, acrylic acid crosslinked polymers.

(2-1) Preparation Step of Aqueous Monomer Solution

The present step is a step of preparing an aqueous solution containing acrylic acid (salt) as the main component (hereinafter referred to as "aqueous monomer solution"). A slurry solution of a monomer may be used within a range in which the fluid retention performance of the resulting water absorbent material such as a water absorbent resin and the like does not decrease, however, this section describes an aqueous monomer solution for convenience.

In addition, the above-described "main component" means that the amount of acrylic acid (salt) used (contained) is, relative to the total monomer (except for an internal crosslinking agent) subjected to polymerization reaction of the water absorbent material such as the water absorbent resin and the like, commonly 50 mol % or more, preferably 70 mol % or more, and more preferably 90 mol % or more (the upper limit is 100 mol %).

(2-2) Polymerization Step

The present step is a step of polymerizing an acrylic acid (salt)-based monomer aqueous solution obtained in the preparation step of the above-described aqueous monomer solution to provide a crosslinked hydrogel polymer (hereinafter referred to as "hydrogel").

An acrylic acid crosslinked polymer with a soluble content of 40 weight % or greater, which is one embodiment of the present invention, can be manufactured by appropriately changing the amount of crosslinking agent or the like, as needed, while referring to the specific requirement of a Test Example or the like based on the descriptions herein. Although not wishing to be bound by any theory, the amount of soluble content decreases, for example, as the amount of crosslinking agent increases.

An acrylic acid crosslinked polymer having a soluble content with a weight average molecular weight of one million Dalton or greater can be manufactured by appropriately changing the amount of crosslinking agent or monomer, or reaction time as needed while referring to the specific requirement of a Test Example or the like based on the description herein. Although not wishing to be bound by any theory, a weight average molecular weight of a soluble content decreases, as the crosslinking agent is increased or the amount of monomer is decreased, for example.

An acrylic acid crosslinked polymer with a fluid retention capacity in physiological saline of 60 g/g or greater and/or a fluid retention capacity in ion exchange water of 600 g/g or greater can be manufactured by appropriately changing the amount of crosslinking agent or the like as needed while referring to the specific requirement of a Test Example or the like based on the description herein. Although not wishing to be bound by any theory, for example, the fluid retention capacity decreases, as the amount of crosslinking agent increases.

An acrylic acid crosslinked polymer with a viscosity upon a 0.12 weight % dispersion in ion exchange water is 100 mPa·s or greater and/or a viscosity upon a 0.72 weight % dispersion in physiological saline is 20 mPa·s or greater, can be manufactured by appropriately changing the amount of crosslinking agent or the like, as needed, while referring to the specific requirement of a Test Example or the like based on the description herein.

(Polymerization Initiator)

Although a polymerization initiator to be used is not particularly limited as it is appropriately selected depending on a particular embodiment of polymerization and the like, examples thereof include pyrolysis-type polymerization initiators, photolysis-type polymerization initiators, redox-based polymerization initiators used in combination with a reducing agent facilitating the decomposition of these polymerization initiators, and the like. Specifically, one type or two or more types of polymerization initiators disclosed in U.S. Pat. No. 7,265,190 are used. From the viewpoints of the handling property of a polymerization initiator and physical properties of the water absorbent material such as water absorbent resin and the like, preferably a peroxide or an azo compound, more preferably a peroxide, and more preferably a persulfate salt are used.

The amount of the polymerization initiator used is, relative to the monomer, preferably 0.001 to 1 mol %, and more preferably 0.001 to 0.5 mol %. In addition, the amount of the reducing agent used is, relative to the monomer, preferably 0.0001 to 0.02 mol %.

Polymerization reaction may be carried out with irradiation of active energy ray, such as a radiation, electron ray, a ultraviolet ray, and the like, instead of the above-described polymerization initiators, and these active energy rays and the polymerization initiator may be used in combination.

(Polymerization Type)

Examples of polymerization types to be applied include, but not particularly limited to, preferably spray droplet polymerization, aqueous solution polymerization, and reverse-phase suspension polymerization, more preferably aqueous solution polymerization and reverse-phase suspension polymerization, and further preferably aqueous solution polymerization from the viewpoints of a water-absorbing property, easiness of polymerization control, or the like. Among these, continuous aqueous solution polymerization is particularly preferable, and both of continuous belt polymerization and continuous kneader polymerization are applied.

As specific polymerization, continuous belt polymerization is disclosed in U.S. Pat. Nos. 4,893,999, 6,241,928, United States Patent Application Publication No. 2005/215734, and the like, and continuous kneader polymerization is disclosed in U.S. Pat. Nos. 6,987,151, 6,710,141, and the like. Adoption of these continuous aqueous solution polymerizations enhances the production efficiency of a water absorbent material such as water absorbent resin and the like.

In addition, examples of preferable forms of the above-described continuous aqueous solution polymerization include a "high-temperature-initiated polymerization" and a "high concentration polymerization". "high-temperature-initiated polymerization" means polymerization started with the temperature of an aqueous monomer solution at preferably 30° C. or more, more preferably 35° C. or more, further preferably 40° C. or more, and particularly preferably 50° C. or more (the upper limit is a boiling point). "High concentration polymerization" means polymerization in a monomer concentration of preferably 30 weight % or more, more preferably 35 weight % or more, further preferably 40 weight % or more, and particularly preferably 45 weight % or more (the upper limit is saturated concentration). These polymerization forms can be used in combination.

In addition, although polymerization can be carried out under air atmosphere, from the viewpoint of the color tone of the resulting water absorbent material such as water absorbent resin and the like, polymerization is preferable to be carried out under atmosphere of an inert gas, such as nitrogen, argon, and the like. In this case, for example, it is preferable to control the oxygen concentration to 1 volume % or less. Meantime, regarding dissolved oxygen in the aqueous monomer solution, it is preferable to be replaced with an inert gas beforehand (for example, dissolved oxygen: less than 1 mg/l).

In addition, foaming polymerization may be selected, which polymerization is carried out with bubble (in particular, the above-described inert gas and the like) dispersed in the aqueous monomer solution.

In addition, during polymerization, the solid content concentration may be allowed to increase. As an index of an increase in such solid content concentration, the degree of an increase in the solid content is defined by the following formula (2). The degree of an increase in the solid content concentration is preferably 1 weight % or more, and more preferably 2 weight % or more.

(The degree of an increase of the solid content (weight %))=(The solid content concentration of a hydrogel after polymerization(weight %))= (The solid content concentration of an aqueous monomer solution(weight %))  [Formula 2]

Wherein the solid content concentration of an aqueous monomer solution is a value obtained from the following formula (3), the components in a polymerization system are an aqueous monomer solution and a graft component, water absorbent material such as a water absorbent resin and the like, and other solid (e.g., water-insoluble fine particle, and the like), and a hydrophobic solvent in reverse-phase suspension polymerization is not included.

(The solid content of an aqueous monomer solution (weight %))=(The weight of (monomer component+graft component+water absorbent material such as water absorbent resin and the like+other solid))/(The weight of components in a polymerization system)×100  [Formula 3]

(2-3) Gel Crushing Step

The present step is a step of gel crushing a hydrogel obtained in the above-described polymerization step, for example, by a screw extruder such as a kneader, a meat chopper, and the like, and a gel crusher such as a cutter mill and the like, to provide a particulate hydrogel (hereinafter referred to as "hydrogel particles"). It should be noted that when the above-described polymerization step is kneader polymerization, the polymerization step and the gel crushing step are carried out at the same time. When hydrogel particles is directly obtained in a polymerization process such as in vapor phase polymerization, reverse-phase suspension polymerization or the like, the gel crushing step may be not carried out.

Regarding gel crushing conditions and forms other than the above-described, the contents disclosed in International Publication No. 2011/126079 are preferably applied to the present invention.

(2-4) Drying Step

The present step is a step of drying a hydrogel particles obtained in the above-described polymerization step and/or the gel crushing step to a desired resin solid content to provide a dry polymer. The resin solid content is obtained from loss on drying (a weight change when 1 g of water absorbent material, such as a water absorbent resin and the like, is heated at 180° C. for 3 hours), and is preferably 80 weight % or more, more preferably 85 to 99 weight %, further preferably 90 to 98 weight %, and particularly preferably 92 to 97 weight %.

Examples of methods of drying the above-described hydrogel particles include, but not particularly limited to, drying by heating, hot-air drying, drying under reduced pressure, fluidized bed drying, infrared ray drying, microwave drying, drum dryer drying, drying by azeotropic dehydration with a hydrophobic organic solvent, high humidity drying using a water steam at a high temperature, and the like. Among these, hot-air drying is preferable from the viewpoint of drying efficiency. More preferable is band drying in which hot-air drying is performed on a ventilated belt.

Drying temperature in the above-described hot-air drying (the temperature of the hot air) is, from the viewpoints of the color tone of water absorbent material such as a water absorbent resin and the like and drying efficiency, preferably 120 to 250° C. and more preferably 150 to 200° C. It should be noted that drying conditions other than the above-described drying temperature, such as the wind velocity of the hot air, drying time, and the like, may be appropriately set depending on the water content and total weight of a hydrogel particles subjected to drying, and the intended resin solid content. In performing band drying, various conditions described in International Publication Nos. 2006/100300, 2011/025012, 2011/025013, and 2011/111657, and the like are appropriately applied.

By selecting the above-mentioned drying temperature and drying time within the above-described range, the CRC (fluid retention capacity) of the resulting water absorbent material such as a water absorbent resin and the like can be made within the desired range (see the following [3]).

(2-5) Pulverization Step, Classification Step

The present step is a step of pulverizing a dry polymer obtained in the above-described drying step (pulverization step) and adjusting it to the particle size within a predetermined range (classification step) to provide powder of a water absorbent material such as a water absorbent resin and the like (powdered water absorbent resin before conducting surface crosslinking is referred to as "water absorbent resin powder" for convenience).

An acrylic acid crosslinked polymer with an average particle diameter (D50) of 10 μm or greater can be manufactured by appropriately changing the opening of a sieve or the like as needed while referring to the specific requirement of a Test Example or the like based on the description herein. Although not wishing to be bound by any theory, for example, the average particle diameter (D50) increases as the area of opening of a sieve increases.

Examples of apparatus used in the pulverization step include high speed rotation type pulverizer such as a roll mill, a hammer mill, a screw mill, a pin mill, and the like, vibration mill, a knuckle-type pulverizer, a cylindrical mixer, and the like. They are used in combination as necessary.

In addition, examples of methods of particle size adjustment in the classification step include, but not particularly limited to, sieve classification using JIS standard sieves (JIS Z8801-1(2000)), air flow classification and the like. It should be noted that the particle size adjustment of water absorbent material such as a water absorbent resin and the like is not limited to the above-described pulverization step and the classification step, but can be appropriately performed in a polymerization step (in particular, reverse-phase suspension polymerization and spray droplet polymerization), and other steps (e.g., granulation step, fine powder recovery step).

The obtained water absorbent material powder such as a water absorbent resin and the like has a weight average particle diameter (D50) of preferably 10 to 800 μm, more preferably 100 to 800 μm, still more preferably 150 to 700 μm, particularly more preferably 200 to 600 μm, and most preferably 200 to 400 μm. Further, the percentage of particles having a particle size less than 150 μm is preferably 10 weight % or less, and the ratio of particles with a particle size of 850 μm or greater is preferably 5 weight % of less, more preferably 3 weight % of less, and still more preferably 1 weight % or less. It should be noted that regarding the lower limit of the percentage of these particles, in any cases, as the lower limit is smaller, it is more preferable. Although 0 weight % is desired, it may be about 0.1 weight %. Further, the logarithmic standard deviation (sigma zeta ($\sigma\zeta$)) of particle size distribution is preferably 0.20 to 0.50, more preferably 0.25 to 0.40, and still more preferably 0.27 to 0.35. It should be noted that these particle sizes are measured using a standard sieve in accordance with measuring methods disclosed in U.S. Pat. No. 7,638,570 and EDANA ERT420.2-02.

The above-mentioned particle sizes are applied to not only a water absorbent resin after surface crosslinking (hereinafter, for convenience, referred to as "water absorbent resin particle" in some cases), but also water absorbent material such as a water absorbent resin and the like as a final product.

(2-6) Surface Crosslinking Step

The present step is a step of providing a portion having further higher crosslinking density for a surface layer (a portion from the surface to several tens of micrometers of the water absorbent material powder such as water absorbent resin and the like) of water absorbent material particles such as a water absorbent resin and the like obtained through the above-described steps. It is composed of a mixing step, a heat treatment step, and a cooling step.

In the surface crosslinking step, since a surface crosslinked water absorbent material such as a water absorbent resin and the like (water absorbent material particle such as water absorbent resin and the like) is obtained by radical crosslinking, surface polymerization, crosslinking reaction with a surface crosslinking agent, and the like on the surface of water absorbent material powder such as a water absorbent resin and the like, it may be appropriately carried out depending on performance required for the water absorbent material such as a water absorbent resin and the like. When a water absorbent material such as a water absorbent resin and the like is utilized as a gelling agent that is primarily for thickening a liquid, there would be less need for surface crosslinking.

(Surface Crosslinking Agent)

Examples of surface crosslinking agents to be used include, but not particularly limited to, organic and inorganic surface crosslinking agents. Among these, from the viewpoints of physical properties of a water absorbent material such as a water absorbent resin and the like and the handling property of a surface crosslinking agent, organic surface crosslinking agents that react with a carboxyl group are preferable. Examples thereof include one type or two or more types of surface crosslinking agents disclosed in U.S. Pat. No. 7,183,456. More specific examples thereof include polyhydric alcohol compounds, epoxy compounds, halo-epoxy compounds, polyamine compounds and condensed compounds with the halo-epoxy compound, oxazoline compounds, oxazolidinone compounds, multivalent metal salts, alkylene carbonate compounds, cyclic urea compounds, and the like.

The amount of the surface crosslinking agent used (the total amount used if a plurality of the agents are used) is, relative to 100 parts by weight of the powder of water absorbent material such as a water absorbent resin and the like, preferably 0.01 to 10 parts by weight, and more preferably 0.01 to 5 parts by weight. Further, the surface crosslinking agent is preferable to be added as an aqueous solution, in which case, the amount of water used is, relative to 100 parts by weight of the powder of water absorbent material such as a water absorbent resin and the like, preferably 0.1 to 20 parts by weight, and more preferably 0.5 to 10 parts by weight. Further, as necessary, when a hydrophilic organic solvent is used, the amount used thereof is, relative to 100 parts by weight of the powder of water absorbent material such as a water absorbent resin and the like, preferably 10 parts by weight or less, and more preferably 5 parts by weight or less.

In addition, each additive added in the below-mentioned "re-humidification step", in an amount of within a range of 5 parts by weight or less, can be mixed with the surface crosslinking agent (aqueous solution) and added, or separately be added in the present mixing step.

(Mixing Step)

The present step is a step of mixing the above-described surface crosslinking agent with the powder of water absorbent material such as a water absorbent resin and the like. Examples of mixing methods of the surface crosslinking agent include, but not particularly limited to, a method of preferably spraying or dropping, more preferably spraying, a surface crosslinking agent solution previously prepared toward the powder of water absorbent material such as a water absorbent resin and the like to mix them.

Examples of apparatus for performing the mixing include, but not particularly limited to, preferably high speed stirring type mixer, and more preferably high speed stirring type continuous mixer.

(Heat Treatment Step)

The present step is a step of heating a mixture obtained in the mixing step to cause crosslinking reaction on a surface of the powder of water absorbent material such as a water absorbent resin and the like. Examples of apparatus for performing the crosslinking reaction include, but not particularly limited to, preferably a paddle dryer. Although the reaction temperature in the crosslinking reaction is appropriately set depending on the type of a surface crosslinking agent to be used, it is preferably 50 to 300° C., and more preferably 100 to 200° C.

(Cooling Step)

The present step is a step, as necessary, provided after the above-described heat treatment step.

Examples of apparatus for performing the cooling include, but not particularly limited to, preferably an apparatus having the same specifications as an apparatus used in the heat treatment step, and more preferably a paddle dryer. The reason is that it can be used as a cooling apparatus by changing a heating medium to a refrigerant. It should be noted that the particle of water absorbent material such as a water absorbent resin and the like obtained in the above-described heat treatment step is, in the cooling step, forcibly cooled to preferably 40 to 80° C., more preferably 50 to 70° C., as necessary.

(2-7) Optional Re-Humidification Step

The present step is a step of adding at least one type of additive selected from the group consisting of the following multivalent metal salt compounds, cationic polymers, chelating agents, inorganic reducing agents, and α-hydroxy-carboxylic acid compounds, to the particle of water absorbent material such as a water absorbent resin and the like obtained in the above-described surface crosslinking step.

It should be noted that since the above-described additive is added as an aqueous solution or a slurry solution, the powder of water absorbent material, such as a water absorbent resin and the like, swells again with water. For this reason, the present step is referred to as "re-humidification step". Moreover, as mentioned above, the additive may be mixed with the powder of water absorbent material such as a water absorbent resin and the like at the same time as the surface crosslinking agent (aqueous solution).

(Multivalent Metal Salt and/or Cationic Polymer)

From the viewpoint of an improvement in water absorption speed, liquid permeability, moisture absorption fluidity, and the like of the resulting water absorbent material such as a water absorbent resin and the like, it is preferable to add a multivalent metal salt and/or a cationic polymer.

As the above-described multivalent metal salt and/or the cationic polymer, specifically, compounds and the amounts used thereof disclosed in "[7] Multivalent metal salt and/or cationic polymer" of International Publication No. 2011/040530 are applied to the present invention.

(2-8) Other Additive-Adding Steps

An additive other than the above-mentioned additives may be added to impart various functions to a water absorbent material such as a water absorbent resin and the like, such as caking resistance, low dust generation and the like. Specific examples of the additives include a surfactant, a compound having a phosphorous atom, an oxidant, an organic reducing agent, a water-insoluble inorganic fine particle, organic powder such as metallic soap and the like, deodorant, antibacterial agent, and the like. It should be noted that compounds disclosed in International Publication No. 2005/075070 are applied as the above-described surfactant, and compounds disclosed in "[5] Water-insoluble inorganic fine particle" of International Publication No. 2011/040530 are applied as the water-insoluble inorganic fine particle.

Since the amount of the additive used (the amount to be added) is appropriately determined depending on its use, it is not particularly limited, but preferably 3 parts by weight or less and more preferably 1 part by weight or less relative to 100 parts by weight of the powder of water absorbent material such as a water absorbent resin and the like. In addition, the additive may be added in a different step from the above-described step.

When the water absorbent material such as a water absorbent resin and the like of the present invention (acrylic acid crosslinked polymer) is used in an application as a gelling agent in particular, a known gelling agent can be added.

Specific examples thereof include water soluble polymeric compounds such as natural polysaccharides, polyacrylamide, polyacrylamide copolymers, polyvinyl alcohol, polyvinyl pyrrolidone, polyalkyleneoxide, 2-acrylamido-2-methylpropane sulfonic acid, acrylic acid or a salt thereof, and the like. Natural polysaccharides are not particularly limited, but are preferably guar gum, sodium carboxymethyl guar, hydroxyethyl guar, hydroxypropyl guar, carboxymethyl hydroxypropyl guar, xanthan gum, locust bean gum, galactomannan, glucomannan, carboxymethyl gum, karaya gum, sodium hydroxymethyl cellulose, sodium carboxymethyl hydroxyethyl cellulose, hydroxymethyl cellulose, hydroxyethyl cellulose, hydroxypropyl starch and the like.

Among them, gaur, glucomannan, galactomannan and their derivatives are particularly preferable since they can increase viscosity of a fluid by adding a relative small amount of one to a water absorbent material as a water absorbent resin and the like. When the polysaccharide coexists with a water absorbent material such as a water absorbent resin and the like, for example, in use of said composition for a fracturing fluid, a proppant would be able to be effectively maintained without using a known crosslinking agent such as sodium tetraborate or zirconium lactate.

(2-9) Other Steps

Other than the above-mentioned steps, a granulation step, a sizing step, a fine powder removing step, a fine powder recycling step, and the like can be provided as necessary. In addition, one type or two or more types of steps of a transportation step, a storage step, a packaging step, a preservation step, and the like may be further included. It should be noted that the "sizing step" includes a fine powder removing step after a surface crosslinking step, and a step of classifying and/or pulverizing if a water absorbent material such as a water absorbent resin and the like aggregates to be larger than the desired size. Moreover, the "fine powder recycling step" includes a step of adding fine powder as it is as in the present invention, and a step of making a large hydrogel therefrom to add it in any of steps for producing a water absorbent material such as a water absorbent resin.

[3] Physical Properties of Acrylic Acid Crosslinked Polymer

Acrylic acid crosslinked polymer obtained by the manufacturing method of one embodiment of the present invention desirably control at least one or more physical properties set forth in the following (3-1) to (3-4), preferably two or more said properties including AAP, more preferably 3 or more, including AAP, and most preferably, all said physical properties within a desirable range.

Further, the shape of an acrylic acid crosslinked polymer obtained by the manufacturing method in one embodiment of the present invention is not particularly limited, but is preferably particulate. This section explains the physical properties of a particulate water absorbent material such as a water absorbent resin and the like as a preferred form. The following physical properties were measured in accordance with the EDANA method unless specifically noted otherwise.

(3-1) Fluid Retention Capacity Without Pressure

The fluid retention capacity without pressure of a water absorbent material such as the acrylic acid crosslinked polymer of the invention and the like is preferably 300 g/g or greater in ion exchange water or 40 g/g or greater in physiological saline, and more preferably 600 g/g or greater in ion exchange water or 60 g/g or greater in physiological saline. The fluid retention capacity without pressure can be controlled with an internal crosslinking agent, surface crosslinking agent, or the like.

(3-2) AAP (Fluid Retention Capacity Under Pressure)

AAP (Fluid Retention Capacity under pressure) of a water absorbent material such as the water absorbent resin of the invention and the like is preferably 25 g/g or less. AAP can be controlled with particle size, the surface crosslinking agent or the like.

(3-3) Particle Size (Particle Size Distribution, Weight Average Particle Diameter (D50), Logarithmic Standard Deviation (Sigma Zeta ($\sigma\zeta$)) of Particle Size Distribution)

Particle size (particle size distribution, weight average particle diameter (D50), logarithmic standard deviation (sigma zeta ($\sigma\zeta$)) of particle size distribution) of a water absorbent material such as the water absorbent resin of the invention and the like is controlled to be the same as the particle size of powder of water absorbent material such as a water absorbent resin and the like before surface crosslinking.

(3-4) Ext (Water Soluble Content)

The Ext (water soluble content) of a water absorbent material, such as the water absorbent resin of the invention and the like, is 10 weight % or greater, and is preferably 15 weight % or greater, 20 weight % or greater, 25 weight % or greater, 30 weight % or greater, 35 weight % or greater, 40 weight % or greater, 45 weight % or greater, 50 weight % or greater, 55 weight % or greater, or 60 weight % or greater. The upper limit thereof is less than 95 weight %, less than 90 weight %, less than 85 weight %, or less than 80 weight %.

Meantime Ext can be controlled with the internal crosslinking agent or the like.

(4) "Normal Temperature"

"Normal temperature" as used herein refers to a temperature at a location where mining is performed, generally in the temperature range of 5 to 40° C.

(5) "High Temperature Condition"

"High temperature condition", as used herein, refers to a temperature at a location where a hydraulic fracturing method is applied such as a shale layer, including temperatures deep underground. This is generally higher than the "normal temperature" in the determination method of the invention, exemplified by 60° C. to 150° C. Examples thereof include 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., and 150° C. The temperature at the depth of 2000 m is 65° C. to 75° C., and the temperature at 3000 m below is about 95° C. to 105° C.

(6) "Fluid Medium"

"Fluid medium", as used herein, refers to a fluid medium for preparing a fracturing fluid used a water absorbent material as a raw material. This is also called an absorbed liquid. A fluid medium is generally water, such as lake water or river water in the area. A fluid medium generally contains minerals. Thus, specific examples of fluid media include fluid media with hardness that matches the hardness of groundwater in the area.

(7) "Viscosity Stabilizes Over Time"

"Viscosity stabilizes over time" as used herein refers to the amount of variation in viscosity over time is at or below or certain value. This indicates that the amount of variation thereof in use as a fracturing fluid is within an acceptable range. For example, when ion exchange water is used as the fluid medium, the amount of variation from the viscosity after 24 hours to the viscosity after 96 hours in a 80° C. heat resistance test of 15% or less, 10% or less, or 5% or less falls under such a state. For example, when physiological saline is used as the fluid medium, the amount of variation from the viscosity after 24 hours to the viscosity after 96 hours in a 80° C. heat resistance test of 15% or less, 10% or less, or 5% or less falls under such a state. Alternative, the amount of variation from the viscosity after 24 hours to the viscosity after 72 hours in a 110° C. heat resistance test in ion exchange water of 15% or less, 10% or less, or 5% or less falls under such a state. Further, the amount of variation from the viscosity after 24 hours to the viscosity after 72 hours in a 110° C. heat resistance test in physiological saline of 15% or less, 10% or less, or 5% or less falls under such a state.

(8) "Suspension Retainable Viscosity"

"Suspension retainable viscosity" as used herein refers to a viscosity that, when measured under a high temperature condition, is stable over time and suitable as a fracturing fluid. Examples of suitable viscosities include viscosities, upon preparation of a 0.12 weight % dispersion in ion exchange water, which are 100 mPa·s or greater and/or viscosities, upon preparation of a 0.72 weight % dispersion in physiological saline, which are 20 mPa·s or greater. Alternatively, a suitable viscosity is a viscosity, upon preparation of a 0.12 weight % dispersion in ion exchange water, which is 200 mPa·s or greater, 300 mPa·s or greater, 400 mPa·s or greater, 500 mPa·s or greater, 600 mPa·s or greater, 700 mPa·s or greater, 800 mPa·s or greater, 900 mPa·s or greater, or 1000 mPa·s or greater, and/or a viscosity, upon preparation of a 0.72 weight % dispersion in physiological saline, which is 30 mPa·s or greater, 40 mPa·s or greater, 50 mPa·s or greater, 60 mPa·s or greater, 70 mPa·s or greater, 80 mPa·s or greater, 90 mPa·s or greater, 100 mPa·s or greater, 200 mPa·s or greater, 300 mPa·s or greater, 400 mPa·s or greater, 500 mPa·s or greater, 600 mPa·s or greater, 700 mPa·s or greater, 800 mPa·s or greater, 900 mPa·s or greater, or 1000 mPa·s or greater.

(9) "Proppant"

"Proppant" in the present invention means a sand-granular substance to support a fracture formed in hydraulic fracturing of a stratum, and is used as a supporting material in the fracture. After pressure-injection is finished, since a proppant supports a fracture to prevent its complete close, a flow channel of a gas from a reservoir layer can be secured. Examples thereof include ceramics.

(10) "Breaking Material"

A material called a breaking agent can be used in order to decompose a water absorbent material such as a water absorbent resin and the like that has been injected into a fracture. "Breaking agent" in the present invention means a material that can decompose (liquefy) a pressure-injected water absorbent material such as water absorbent resin and the like in hydraulic fracturing of a stratum. After a fracture is formed, a breaking agent can decompose, liquefy, or deteriorate a water absorbent material such as a water absorbent resin and the like in the fracture by injection into the fracture.

(11) Representative Description of Hydraulic Fracturing Technique of a Stratum

The hydraulic fracturing technique is a technique that application of high pressure to fluid filling in a well artificially breaks a reservoir rock near the well and a flow channel of the fluid is secured by artificially forming/extending a fracture into a reservoir layer. The generated fracture (crack) can improve the permeability (ease of a fluid's flow) in the vicinity of the well, and expansion of effective inflow cross-section to the well can enhance the productivity of the well.

The illustrative procedure of the hydraulic fracturing technique is as follows: 1. pressure-injecting high viscosity fluid (gel) from a perforated portion to fracture a rock that is a reservoir layer, to form a fracture; 2. keeping pressure-injection of the gel to make the length and width of the fracture larger; 3. gradually mixing a sand-granular substance, called proppant, with the gel and pressure-injecting them in order to support the formed fracture semipermanently; 4. gradually increasing the concentration of the proppant; 5. on completion of carrying a defined amount of the proppant, stopping a pressure-injection pump; 6. since the pressured-injected gel is decomposed by heat and permeates into the reservoir layer, the formed fracture intends to gradually close, however, since the proppant supports the fracture to prevent it from completely closing, the flow channel of a gas is secured; and 7. a gas that has accumulated in a small gap of the reservoir layer flows into the well through the fracture, and the economical productivity can be secured. It is necessary that the generated fracture is hindered closing and is maintained over a long period of time. For this reason, a granular object called proppant is injected into the arising fracture. In order to generate and maintain a suitable fracture, it is necessary to appropriately design pressure-injected fluid and a proppant. The efficiency of the pressure-injected fracturing fluid can be defined as in the following formula.

Fluid efficiency=(Fracture volume when closed)/(The volume of the fracturing fluid pressure-injected)

The representative procedure of a hydraulic fracturing operation is as follows.

<Typical Procedure of a Hydraulic Fracturing Operation>

(1) Fracturing Operation [Fracture Formation, Fracture Extension]

Pressured injection of fluid: pre-pad (high viscosity fluid, for generating a fracture), pad (gel fluid, for extending a fracture), and proppant-transporting fluid (the mixture of high viscosity fluid and a proppant)

Monitoring of closure of a well and pressure behavior (fracture closure)

(2) Post-Fracturing Operation

Well cleaning (bond-breaking in a polymer of fracturing fluid, back-flow) In order to know the direction of a generated fracture, a fracturing sound at a time of fracture extension (AE: Acoustic Emission) is monitored. A three-dimensional seismometer is installed on an adjacent well or a hydraulically fractured well, the sound source of AE is investigated, and a technique to investigate the spread of a fracture (microseismic technique) is also used. The selection of the material quality and particle size of a proppant is important. The diameter of a proppant should be equal to or less than about one-fourth of the width of a generated fracture. If it is equal to or greater than that, the possibility of screen-out (exclusion from the inside of the fracture) is higher. Further, points to note in the hydraulic fracturing operation are as follows.

<Points to Note in the Hydraulic Fracturing Operation>
(1) Fracturing Fluid
It is broadly classified into the following three types.
1. A polymer aqueous solution (moderate viscosity).
2. A polymer aqueous solution and crosslinked (high viscosity).
3. Water-oil emulsion.

Furthermore, major features that should be had as fracturing fluid are the following four points.
1. Making a fracture under a stratum condition and having a viscosity that can transport a support material.
2. Suitable fluid efficiency (the leak off is small).
3. Compatibility with a stratum or formation water.
4. Quick decomposition after the treatment.

(2) Support Material

After completion of the hydraulic fracturing operation, blocking pressure from the fissure surface is applied to a support material. However, it is important that it does not break the fissure to bury a support material in a stratum.

(3) Pressure for Pressure-Injection and Necessary Horsepower (Pressure for Pressure-Injection at a Pit Mouth/Discharge pressure of a pump)=(fracture pressure)+(friction loss in a pipe)+(pressure loss at a perforated portion)−(hydrostatic pressure).

The necessary horsepower of a pump is calculated by the formula: Pressure for pressure-injection at a pit mouth× Pressure-injection speed, and the number of necessary pump is determined in view of the efficiency.

(4) Securing the Path of Fracturing Fluid

Acid treatment is commonly performed as pretreatment of hydraulic fracturing. Cleaning treatment of a perforation is also performed. In the second-half part of the cleaning treatment, it is effective to confirm that the fracturing pressure is not much different from a predicted value.

(5) Pressure-Injection Speed

Before hydraulic fracturing, many data are estimated values. However, by securing enough pressure-injection speed, any troubles due to uncertainty can be solved.

(6) Pressure-Injection Operation

Pressure-injection is started with a low viscosity acid (15% hydrochloric acid) or brine (2% potassium chloride) as a pre-pad. Subsequently, fracturing fluid to be pressure-injected (which fluid does not contain a support material) is called pad, and its amount has a great influence on accomplishment of the operation. The pad always penetrates to the deepest portion in a fissure, and destroys a stratum by pressure as if propagated from the subsequent. However, when the pad is consumed by leak off or the like, the development of a fissure stops, and sand of a support material precipitates in a well to cause the stoppage of the operation. It is said that at least 20% of the fracture fluid amount previously determined should be used as the pad. In the case of a gas layer, the proportion of the pad is increased. It is important to improve the conductivity in the vicinity of a well, and reduce loss due to burying sand in a stratum.

Disclosure of Preferred Embodiment

Preferable embodiments of the present invention are described below. Embodiments below are provided only for better understanding of the present invention and it should be understood that the scope of the present invention is not limited to the description below. It is, thus apparent that those who are skilled in the art can appropriately modify the present invention within the scope of the present invention in view of the description of the present specification.

Moreover, it will be understood that the following embodiments of the present invention can be used alone or in combination thereof.

In one aspect, the present invention provides an acrylic acid crosslinked polymer, wherein an amount of a soluble content is 40 weight % or greater. Although not wishing to be bound by any theory, this is because such an acrylic acid crosslinked polymer can exhibit excellent thickening behavior when used as a water absorbent material such as a water absorbent resin and the like. Alternatively, an acrylic acid crosslinked polymer, wherein an amount of a soluble content is 45 weight % or greater, 50 weight % or greater, 55 weight % or greater, 60 weight % or greater, 65 weight % or greater, 70 weight % or greater, 75 weight % or greater, 80 weight % or greater, 85 weight % or greater, 90 weight % or greater, 95 weight % or greater, 99 weight % or greater, or less than 100 weight % is provided.

In another aspect, the amount of a soluble content of an acrylic acid crosslinked polymer with a particle size greater than 300 µm and less than 425 µm (Pass 425 µm/On 300 µm) is measured. Although not wishing to be bound by any theory, this is because a comparison can be made thereby without considering the difference in performance arising due to difference in particle sizes. Even when all the particles are measured, the amount of soluble content of the acrylic acid crosslinked polymer in one embodiment of the present invention is 40 weight % of greater, 45 weight % or greater, 50 weight % or greater, 55 weight % or greater, 60 weight % or greater, 65 weight % or greater, 70 weight % or greater, 75 weight % or greater, 80 weight % or greater, 85 weight % or greater, 90 weight % or greater, 95 weight % or greater, 99 weight % or greater, or less than 100 weight %. Although not wishing to be bound by any theory, hardly any difference is observed in the value of the amount of soluble content between cases where an acrylic acid crosslinked polymer with a particle size greater than 300 µm and less than 425 µm (Pass 425 µm/On 300 µm) was measured and cases where the all particles were measured. In practice, the value for Pass 425 µm/On 300 µm can be used similarly to a measurement value for all particles.

In one preferred embodiment, a weight average molecular weight of the soluble content is one million Dalton or greater. Although not wishing to be bound by any theory, this is because an excellent thickening behavior can be exhibited thereby when used as a water absorbent material such as a water absorbent resin and the like. Alternatively, the weight average molecular weight of the soluble content is 1.2 million Dalton or greater, 1.4 million Dalton or greater, 1.6 million Dalton or greater, 1.8 million Dalton or greater, 2 million Dalton or greater, 2.5 million Dalton or greater, 3 million. Dalton or greater, 4 million Dalton or greater, or 5 million Dalton or greater.

In another aspect, the weight average molecular weight of the soluble content is measured for an acrylic acid crosslinked polymer with a particle size of greater than 300 µm and less than 425 µm (Pass 425 µm/On 300 µm). Although not wishing to be bound by any theory, this is because a comparison can be made thereby without considering the difference in performance due to difference in particle sizes. Even when all particles are measured, the weight average molecular weight of soluble content of an acrylic acid crosslinked polymer in one embodiment of the present invention is 1 million Dalton or greater, 1.2 million Dalton or greater, 1.4 million Dalton or greater, 1.6 million Dalton or greater, 1.8 million Dalton or greater, 2 million Dalton or greater, 2.5 million Dalton or greater, 3 million Dalton or greater, 4 million Dalton or greater, or 5 million Dalton or greater. Although not wishing to be bound by any theory, in practice, the value of the weight average molecular weight of the soluble content for Pass 425 μm/On 300 μm can be used similarly to a measurement value for the entire particle.

In another preferred embodiment, a fluid retention capacity in physiological saline is 40 g/g or greater and preferably 60 g/g or greater, and/or a fluid retention capacity in ion exchange water is 300 g/g or greater and preferably 600 g/g or greater. Alternatively, the fluid retention capacity in physiological saline is 40 g/g or greater, 45 g/g or greater, 50 g/g or greater, 55 g/g or greater, 60 g/g or greater, 65 g/g or greater, 70 g/g or greater, 75 g/g or greater, 80 g/g or, greater, 85 g/g or greater, 90 g/g or greater, 100 g/g or greater, 110 g/g or greater, 120 g/g or greater, 130 g/g or greater, 140 g/g or greater, 150 g/g or greater, or 200 g/g or greater, and/or the fluid retention capacity in ion exchange water is 300 g/g or greater, 400 g/g or greater, 500 g/g or greater, 600 g/g or greater, 700 g/g or greater, 800 g/g or greater, 900 g/g or greater, 1000 g/g or greater, 1100 g/g or greater, 1200 g/g or greater, 1300 g/g or greater, 1400 g/g or greater, 1500 g/g or greater, 1600 g/g or greater, 1700 g/g or greater, 1800 g/g or greater, 1900 g/g or greater, or 2000 g/g or greater.

In another aspect, the fluid retention capacity in physiological saline is measured for an acrylic acid crosslinked polymer with a particle size of greater than 300 μm and less than 425 μm (Pass 425 μm/On 300 μm). Although not wishing to be bound by any theory, this is because a comparison can be made thereby without considering the difference in performance due to difference particle sizes. Even when all particles are measured, the fluid retention capacity in physiological saline of an acrylic acid crosslinked polymer, in one embodiment of the present invention, is 40 g/g or greater, 45 g/g or greater, 50 g/g or greater, 55 g/g or greater, 60 g/g or greater, 65 g/g or greater, 70 g/g or greater, 75 g/g or greater, 80 g/g or greater, 85 g/g or greater, 90 g/g or greater, 100 g/g or greater, 110 g/g or greater, 120 g/g or greater, 130 g/g or greater, 140 g/g or greater, 150 g/g or greater, or 200 g/g or greater, and/or the fluid retention capacity in ion exchange water is 300 g/g or greater, 400 g/g or greater, 500 g/g or greater, 600 g/g or greater, 700 g/g or greater, 800 g/g or greater, 900 g/g or greater, 1000 g/g or greater, 1100 g/g or greater, 1200 g/g or greater, 1300 g/g or greater, 1400 g/g or greater, 1500 g/g or greater, 1600 g/g or greater, 1700 g/g or greater, 1800 g/g or greater, 1900 g/g or greater, or 2000 g/g or greater. Although not wishing to be bound by any theory, hardly any difference is observed in the fluid retention capacities between cases where an acrylic acid crosslinked polymer with a particle size greater than 300 μm and less than 425 μm (Pass 425 μm/On 300 μm) was measured and cases where all particles were measured. In practice, the value for Pass 425 μm/On 300 μm can be used similarly to a measurement value for all of the particles.

In another preferred embodiment, a viscosity upon a 0.12 weight % dispersion in ion exchange water is 100 mPa·s or greater and/or a viscosity upon a 0.72 weight % dispersion in physiological saline is 20 mPa·s or greater. Alternatively, the viscosity upon preparing a 0.12 weight % dispersion in ion exchange water is 200 mPa·s or greater, 300 mPa·s or greater, 400 mPa·s or greater, 500 mPa·s or greater, 600 mPa·s or greater, 700 mPa·s or greater, 800 mPa·s or greater, 900 mPa·s or greater, or 1000 mPa·s or greater and/or the viscosity upon a 0.72 weight % dispersion in physiological saline is 30 mPa·s or greater, 40 mPa·s or greater, 50 mPa·s or greater, 60 mPa·s or greater, 70 mPa·s or greater, 80 mPa·s or greater, 90 mPa·s or greater, 100 mPa·s or greater, 200 mPa·s or greater, 300 mPa·s or greater, 400 mPa·s or greater, 500 mPa·s or greater, 600 mPa·s or greater, 700 mPa·s or greater, 800 mPa·s or greater, 900 mPa·s or greater, or 1000 mPa·s or greater.

In another preferred embodiment, the polymer is a particle with an average particle diameter (D50) of 10 μm or greater. Although not wishing to be bound by any theory, this is because an excellent thickening behavior can be exhibited thereby when used as a water absorbent material such as a water absorbent resin and the like. The average particle diameter (D50) of the polymer is not limited to this value, for example, but is 10 μm, 20 μm, 30 μm, 40 μm, 50 μm, 60 μm, 70 μm, 80 μm, 90 μm, 100 μm, 150 μm, 200 μm, 250 μm, 300 μm or greater, and 800 μm, 750 μm, 700 μm, 650 μm, 600 μm, 550 μm, 500 μm or less.

In one aspect, the present invention provides a gelation thickening agent comprising the above-described acrylic acid crosslinked polymer.

In one aspect, the present invention provides a water absorbent agent for a fracturing fluid in a hydraulic fracturing method, comprising the above-described acrylic acid crosslinked polymer.

In one preferred embodiment, a neutralization rate of the acrylic acid crosslinked polymer is greater than 75 mole %. Alternatively, the neutralization rate of the acrylic acid crosslinked polymer is greater than 80 mole %, greater than 85 mole %, greater than 90 mole %, greater than 95 mole %, greater than 99 mole %, or 100 mole %. Although not wishing to be bound by any theory, this is because a neutralization rate greater than 75 mole % results in high heat resistance.

In one aspect, the present invention provides an additive for a water absorbent agent for a fracturing fluid in a hydraulic fracturing method, comprising a chelating agent.

In one preferred embodiment, the chelating agent is 0.01 weight % or greater with respect to the water absorbent agent. Alternatively, the chelating agent is 0.1 weight % or greater. Alternatively, the chelating agent is 0.01 weight % or greater, 0.02 weight % or greater, 0.03 weight % or greater, 0.04 weight % or greater, 0.05 weight % or greater, 0.06 weight % or greater, 0.07 weight % or greater, 0.08 weight % or greater, 0.09 weight % or greater, 0.1 weight % or greater, 0.2 weight % or greater, 0.3 weight % or greater, 0.4 weight % or greater, 0.5 weight % or greater, 0.6 weight % or greater, 0.7 weight % or greater, 0.8 weight % or greater, 0.9 weight % or greater, or 1 weight % or greater. The upper limit may be appropriately determined from the relationship with other components of a fracturing fluid. One guideline amount is 200 weight % of less.

In one aspect, the present invention provides an additive for a water absorbent agent for a fracturing fluid in a hydraulic fracturing method, comprising a raw material of the acrylic acid crosslinked polymer and a crosslinking agent.

In one aspect, the present invention provides a kit for a water absorbent agent for a fracturing fluid in a hydraulic fracturing method, comprising an acrylic acid crosslinked polymer comprising a chelating agent and/or a chelating agent and an acrylic acid crosslinked polymer. Any acrylic acid crosslinked polymer can be used as the acrylic acid crosslinked polymer, but preferably has the features defined herein.

In one preferred embodiment, the average particle diameter (D50) of the acrylic acid crosslinked polymer is characterized in being 150 to 1000 μm.

In one preferred embodiment, the chelating agent is selected from diethylenetriamine pentaacetic acid or a salt thereof.

In one preferred embodiment, the crosslinking agent is triallyl isocyanurate. Although not wishing to be bound by any theory, this is because heat resistance increases due to a crosslinking point broken by heat.

In one aspect, the present invention provides a hydraulic fracturing method comprising performing hydraulic fracturing using a water absorbent agent for a fracturing fluid, comprising the above-described acrylic acid crosslinked polymer.

In one preferred embodiment, a neutralization rate of the acrylic acid crosslinked polymer is greater than 75 mole %. Alternatively, the neutralization rate of the acrylic acid crosslinked polymer is greater than 80 mole %, greater than 85 mole %, greater than 90 mole %, greater than 95 mole %, greater than 99 mole %, or 100 mole %. Although not wishing to be bound by any theory, this is because a neutralization rate of greater than 75 mole % results in a high heat resistance.

In one aspect, the present invention provides a hydraulic fracturing method comprising performing hydraulic fracturing using an additive for a water absorbent agent for a fracturing fluid, comprising a chelating agent.

In one preferred embodiment, the chelating agent is 0.01 weight % or greater with respect to the water absorbent agent. Alternatively, the chelating agent is 0.1 weight % or greater. Alternatively, the chelating agent is 0.01 weight % or greater, 0.02 weight % or greater, 0.03 weight % or greater, 0.04 weight % or greater, 0.05 weight % or greater, 0.06 weight % or greater, 0.07 weight % or greater, 0.08 weight % or greater, 0.09 weight % or greater, 0.1 weight % or greater, 0.2 weight % or greater, 0.3 weight % or greater, 0.4 weight % or greater, 0.5 weight % or greater, 0.6 weight % or greater, 0.7 weight % or greater, 0.8 weight % or greater, 0.9 weight % or greater, or 1 weight % or greater. The upper limit may be appropriately determined from the relationship with other components of a fracturing fluid. One guideline amount is 200 weight % of less.

In one aspect, the present invention provides a hydraulic fracturing method comprising performing hydraulic fracturing using an additive for a water absorbent agent for a fracturing fluid, comprising a raw material of the above-described acrylic acid crosslinked polymer and a crosslinking agent.

In one aspect, the present invention provides a hydraulic fracturing method comprising performing hydraulic fracturing using a kit for a water absorbent agent for a fracturing fluid, comprising an acrylic acid crosslinked polymer comprising a chelating agent and/or a chelating agent and an acrylic acid crosslinked polymer. Any acrylic acid crosslinked polymer can be used as the acrylic acid crosslinked polymer, but preferably has the features defined herein.

In one preferred embodiment, the chelating agent is selected from diethylenetriamine pentaacetic acid or a salt thereof.

In one preferred embodiment, the crosslinking agent is triallyl isocyanurate.

In one aspect, the present invention provides a method of adjusting a viscosity of a fracturing fluid in a hydraulic fracturing method, comprising the steps: A) measuring a metal cation type and an amount thereof in water, which is to be subjected to viscosity adjustment; B) selecting a type and amount of an acrylic acid crosslinked polymer so that a viscosity required for fracturing in the hydraulic fracturing method is obtained, based on the metal cation type, and the amount thereof, and the pH; and C) adjusting the viscosity of the fracturing fluid using the selected type and amount of the acrylic acid crosslinked polymer.

In one preferred embodiment, the type and/or amount of the polymer is determined based on a soluble content.

Another preferred embodiment is characterized by further taking into consideration a weight average molecular weight of the soluble content of the polymer.

Another preferred embodiment is characterized by further adjusting a viscosity using a chelating agent.

In one aspect, the present invention provides a method of determining a water absorbent material that is suitable as a fracturing fluid in a hydraulic fracturing method. A fracturing fluid is affected by various factors. In order to satisfy the required properties, it is necessary to determine a suitable water absorbent material.

The present invention for determining a water absorbent material that is suitable as a fracturing fluid in a hydraulic fracturing method comprises: 1) measuring, under a normal temperature, the relationship between the amount of a polymer in the material and a viscosity of the polymer in a fluid medium; 2) determining an amount of the polymer at which the viscosity is at or greater than a predetermined viscosity; 3) adding a variable amount of a chelating agent to the polymer with a certain amount satisfying the condition determined in 2) and measuring a change in viscosity over time in the fluid medium, under a predetermined high temperature condition; 4) determining an amount of the chelating agent when the viscosity become stabilized over time based on measurement in 3); and 5) employing the certain amount of the polymer and the amount of the chelating agent when the viscosity become stabilized in 4) if the viscosity measured in 3) is a suspension retainable viscosity, but not if the viscosity is not a suspension retainable viscosity.

A water absorbent material that is suitable as a fracturing fluid in a hydraulic fracturing method may be any material with a property required in a fracturing fluid in a hydraulic fracturing method. A material with a required property and a polymer used therein can be determined by the present invention, so that any material or polymer can be used. Examples thereof include water absorbent resins, thickeners, water absorbent crosslinked polymers, and the like. Specific examples include crosslinked polymers such as polyacrylic acid, sodium polyacrylate, and polyacrylamide.

The normal temperature, as used herein, is a temperature at a location where mining is performed, which can be appropriately determined in accordance with the circumstances of the surroundings to which a hydraulic fracturing method is applied. Mining sites for natural resources such as shale gas are outdoors. The temperature at a mining site varies depending on various factors, such as latitude, altitude, season, weather, or daylight hours. Generally, it is a temperature in the range of 5 to 40° C. The viscosity required for a fracturing fluid in a hydraulic fracturing method can vary depending on the temperature. Thus, it is preferable to determine a water absorbent material at the normal temperature of the location where the mining is to be performed.

The method of the invention determines the relationship between the amount and viscosity of a polymer under normal temperature conditions and determine the amount of chelating agent added at which the change in viscosity over time stabilizes under a high temperature condition as a fracturing fluid. The amount of polymer can be determined at a normal temperature, and the amount of chelating agent required for stability under a high temperature condition can be readily determined. Thus, a water absorbent material that is suitable as a fracturing fluid in a hydraulic fracturing method can be readily determined.

A fluid medium in the present invention is a fluid medium for preparing a water absorbent material polymer into a fracturing fluid. Thus, any fluid (typically water) may be used. Water such as lake water or river water in the area is generally used from the viewpoint of economic efficiency. The viscosity required for a fracturing fluid in a hydraulic fracturing method can vary depending on the components such as salt in a fluid medium used. Thus, it is necessary to determine a water absorbent material using a fluid medium to be used. In one embodiment, the fluid medium is water used in the hydraulic fracturing method or water having hardness that is equivalent to that of said water. In a certain embodiment, physiological saline may be used, but a fluid medium is not limited thereto.

A predetermined viscosity considered essential at normal temperature can be readily determined while considering the use as a fracturing fluid. The viscosity may be the same or different from the viscosity required under a high temperature condition. If the viscosity can be stabilized at a viscosity required under a high temperature condition, a predetermined viscosity can be set to any viscosity while taking into consideration the manipulability thereof or the like. In one embodiment, a predetermined viscosity required at normal temperatures is set to a viscosity required under a high temperature condition. In one embodiment, a predetermined viscosity required at normal temperatures is set at a viscosity that is higher than a viscosity required under a high temperature condition. In one embodiment, a predetermined viscosity required at normal temperature is set to a lower viscosity than a viscosity required under a high temperature condition.

A high temperature as used herein is a temperature at a location where a hydraulic fracturing method is applied, such as a shale layer. Such a temperature can be appropriately determined by those skilled in the art. In this regard, a high temperature does not necessarily need to be exactly the same temperature as the mining location. A temperature in the vicinity (e.g., ±10° C., ±5° C., or the like) can be appropriately used. The temperature at a depth of 2000 m is 65° C. to 75° C., and the temperature at 3000 m below is about 95° C. to 105° C. The required high temperature condition varies depending on the location where a natural resource such as shale gas is present. For example, a high temperature is 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., or 150° C.

In the present invention, a chelating agent can be used to stabilize a change in viscosity over time in a fluid medium of a water absorbent material at high temperatures. Chelating agents may be added to a water absorbent material or may be contained in an absorbed liquid.

A change in viscosity over time can be measured by measuring the viscosity for any two or more points in time. It may be a time within a range that is used as a fracturing fluid. For convenience of determination, a certain time may be determined. Examples of times that can be used include, but are not limited to, 1 hour, 3 hours, 5 hours, 10 hours, 12 hours, 24 hours, 36 hours, 48 hours, 60 hours, 72 hours, 96 hours or the like. Generally, viscosities at any two points in time are determined. When viscosities at three of more points are measured, viscosities at any two points may be selected for determination.

It is sufficient, as long as the amount of variation thereof in use as a fracturing fluid is within an acceptable range. The viscosity required as a fracturing fluid (suspension retainable viscosity) is readily understood by those skilled in the art.

In a preferred embodiment, a suitable viscosity as a fracturing fluid is a viscosity, upon preparation of a 0.12 weight % dispersion in ion exchange water, which is 100 mPa·s or greater and/or a viscosity, upon preparation of a 0.72 weight % dispersion in physiological saline, which is 20 mPa·s or greater. Alternatively, the suitable viscosity is a viscosity, upon preparation of a 0.12 weight % dispersion in ion exchange water, which is 200 mPa·s or greater, 300 mPa·s or greater, 400 mPa·s or greater, 500 mPa·s or greater, 600 mPa·s or greater, 700 mPa·s or greater, 800 mPa·s or greater, 900 mPa·s or greater, or 1000 mPa·s or greater, and/or a viscosity, upon preparation of a 0.72 weight % dispersion in physiological saline, which is 30 mPa·s or greater, 40 mPa·s or greater, 50 mPa·s or greater, 60 mPa·s or greater, 70 mPa·s or greater, 80 mPa·s or greater, 90 mPa·s or greater, 100 mPa·s or greater, 200 mPa·s or greater, 300 mPa·s or greater, 400 mPa·s or greater, 500 mPa·s or greater, 600 mPa·s or greater, 700 mPa·s or greater, 800 mPa·s or greater, 900 mPa·s or greater, or 1000 mPa·s or greater.

In a preferred embodiment, the above-described method comprising 6) repeating 3) to 5) if the viscosity measured in 3) is not a suspension retainable viscosity in 5).

In one embodiment, the present invention comprises measuring or selecting a fluid retention capacity of a water absorbent resin. The fluid retention capacity of a water absorbent resin can affect the viscosity of a fracturing fluid.

In one embodiment, the present invention further comprises performing a precipitation test using a proppant particle. The test can confirm the usability as a fracturing fluid.

In one embodiment, a concentration of a chelating agent that is used in a method of determining a water absorbent material and suitable as a fracturing fluid is 0.01 weight % of greater with respect to a polymer in the water absorbent material. Alternatively, the chelating agent is 0.1 weight % or greater. Alternatively, the chelating agent is 0.01 weight % or greater, 0.02 weight % or greater, 0.03 weight % or greater, 0.04 weight % or greater, 0.05 weight % or greater, 0.06 weight % or greater, 0.07 weight % or greater, 0.08 weight % or greater, 0.09 weight % or greater, 0.1 weight % or greater, 0.2 weight % or greater, 0.3 weight % or greater, 0.4 weight % or greater, 0.5 weight % or greater, 0.6 weight % or greater, 0.7 weight % or greater, 0.8 weight % or greater, 0.9 weight % or greater, or 1 weight % or greater. The upper limit may be appropriately determined from the relationship with other components of a fracturing fluid. One guideline amount is 200 weight % of less.

As the chelating agent of the invention, a polymeric compound or a non-polymeric compound are preferred, especially, non-polymeric compounds are preferred, and specifically a compound selected from an amino multivalent carboxylic acid, organic multivalent phosphoric acid, inorganic multivalent phosphoric acid, and amino multivalent phosphoric acid, from the viewpoint of the effect. From the viewpoint of the effect, the molecular weight of the chelating agent is preferably 100 to 5000 and more preferably 200 to 1000.

In this regard, multivalent refers to having multiple functional groups in a single molecule, preferably 2 to 30, more preferably 3 to 20 or 4 to 10 functional groups. Further, such chelating agents are preferably a water soluble chelating agent, specifically a water soluble chelating agent which dissolves in 100 g of water (25° C.) at 1 g or more, more preferably at 10 g or more.

Examples of the above-described amino multivalent carboxylic acid include iminodiacetic acid, hydroxyethyl iminodiacetic acid, nitrilotriacetic acid, nitrilotripropionic acid, ethylenediamine tetraacetic acid, diethylenetriamine pentaacetic acid, triethylenetetraamine hexaacetic acid, trans-1,2-diaminocyclohexane tetraacetic acid, N,N-bis(2-hydroxyethyl)glycine, diaminopropanol tetraacetic acid, ethylenediamine dipropionic acid, hydroxyethylenediamine triacetic acid, glycoletherdiamine tetraacetic acid, diaminopropane tetraacetic acid, N,N'-bis(2-hydroxybenzyl)ethylenediamine-N,N'-diacetic acid, 1,6-hexamethylenediamine-N,N,N',N'-4 tetraacetic acid, salts thereof, and the like.

Examples of the above-described organic multivalent phosphoric acid include nitriloacetic acid-di(methylene phosphinic acid), nitrilodiacetic acid (methylene phosphinic acid), nitriloacetic acid-β-propionic acid-methylene phosphonic acid, nitrilotris(methylene phosphonic acid), 1-hydroxyethylidenediphosphonic acid, and the like. Meantime, examples of the above-described inorganic multivalent phosphoric acid include pyrophosphoric acid, tripolyphosphoric acid, salts thereof, and the like.

Furthermore, examples of the above-described amino multivalent phosphoric acid include ethylenediamine-N,N'-di(methylene phosphinic acid), ethylenediamine tetra(methylene phosphinic acid), cyclohexanediamine tetra(methylenephosphonic acid), ethylenediamine-N,N'-diacetic acid-N,N'-di(methylene phosphonic acid), ethylenediamine-N,N'-di(methylene phosphonic acid), ethylenediamine tetra (methylene phosphonic acid), polymethylenediamine tetra (methylene phosphonic acid), diethylenetriamine penta (methylenephosphonic acid), salts thereof, and the like.

Preferred examples of salts include monovalent salts, especially sodium salts, potassium salts, other alkali metal salts, ammonium salts, amine salts, and the like.

In one aspect, the present invention provides a method of manufacturing a fracturing fluid in a hydraulic fracturing method. The method comprises 1) to 5) or 1) to 6) in the above-described method of determining a water absorbent material that is suitable as a fracturing fluid in a hydraulic fracturing method and 7) manufacturing a fracturing fluid using the certain amount of the polymer and the amount of the chelating agent. A fracturing fluid having a viscosity stabilized over time under a high temperature condition can be manufactured. Once a suitable fracturing fluid is determined, the fracturing fluid can be similarly manufactured and repeatedly used.

In one aspect, the present invention provides a hydraulic fracturing method comprising performing hydraulic fracturing using the above-described fracturing fluid. Once a suitable fracturing fluid is determined by the above-described determination method, hydraulic fracturing can be performed using a fracturing fluid with such components.

Reference including scientific literature, patents, patent applications, and the like cited herein is incorporated herein by reference in its entirety at the same level as the case where each reference is specifically described.

As above, the present invention has been described with reference to preferable embodiments for easy understanding. Hereinafter, the present invention will be described based on test examples, however, the above description and the following test examples are provided only for illustrative purpose and are not provided for the purpose of limiting the present invention. Therefore, the scope of the present invention is not limited by the embodiments or the test examples specifically described in the present specification, but is limited only by the claims.

EXAMPLES

According to the following test examples, the present invention is more specifically described. However, the present invention is not construed limitedly to them, and test examples obtained by appropriately combining technical means disclosed in respective test examples also shall fall within the scope of the present invention.

It should be noted that electrical machinery and apparatus used in the test examples (including the physical property measurement of a water absorbent material such as a water absorbent resin and the like) used a 200 V or 100 V power source unless specified otherwise. Further, various physical properties of the a water absorbent material such as a water absorbent resin of the present invention and the like were measured under a condition of room temperature (20 to 25° C.) and a relative humidity of 40%±10% RH unless specified otherwise.

Further, "liter" may be expressed as "l" or "L", and "weight %" may be expressed as "wt %" for convenience. Furthermore, in the measurement of a trace constituent, being equal to or less than the detection limit is expressed as "N.D." (Not Detected).

[Determination of Physical Properties of Water Absorbent Material Such as Water Absorbent Resin and the Like]

(a) Fluid Retention Capacity 0.20 g of water absorbent resin was uniformly placed in a bag made of unwoven fabric (60 mm×60 mm) and was immersed in significantly excessive amount (100 g or greater) of an aqueous solution with a predetermined salt content or ion exchange water. In addition, the bag was pulled out after 30 minutes and drained for 3 minutes using a centrifuge at 250 G. The weight W2 (g) of the bag was then measured.

At a salt concentration of less than 0.01 weight % (including only ion exchange water), the above-described weight W2 (g) of the bag exceeds 15 (g) in some cases. In such a case, the test was performed at 0.01 g of the water absorbent resin placed in said bag made of unwoven fabric.

The same operation was performed without using a water absorbent resin (water absorbent agent), and the weight W1 (g) at that time was determined. From the weights W1 and W2, the fluid retention capacity (g/g) was calculated in accordance with the following (Formula 4).

Fluid retention capacity (g/g)=(weight $W2$ (g)–weight $W1$ (g)–weight of water absorbent resin (g))/weight of water absorbent resin (g)  (Formula 4)

(b) AAP (Fluid Retention Capacity Under Pressure)

The AAP (Fluid Retention Capacity under pressure) of a water absorbent material such as a water absorbent resin of the invention and the like was measured in accordance with the EDANA method (ERT442.2-02).

(c) Particle Size (Particle Size Distribution, Weight Average Particle Diameter (D50), Logarithmic Standard Deviation (σζ) of Particle Size Distribution)

Particle size (particle size distribution, weight average particle diameter (D50), logarithmic standard deviation (σζ) of particle size distribution) of a water absorbent material such as the water absorbent resin of the invention and the like was determined in accordance with "(3) Mass-Average Particle Diameter (D50) and Logarithmic Standard Deviation (σζ) of Particle Diameter Distribution" as described in columns 27 and 28 of U.S. Pat. No. 7,638,570.

(d) Ext (Water Soluble Content)

Ext (water soluble content) of a water absorbent material such as the water absorbent resin of the invention and the like was determined in accordance with the EDANA method (ERT470.2-02).

(e) Weight Average Molecular Weight of Water Soluble Content

The weight average molecular weight of water soluble content is a value of the weight average molecular weight of the polymer dissolved in the aforementioned Ext measurement operation, which is determined by GPC (Gel Permeation Chromatography). Such GPC measurement is explained below.

The GPC was performed with the use of TDA302 (Registered Trademark) available from VISCOTECH CO., LTD. This instrument is constituted by a size exclusion chromatograph, a refractive index detector, a light diffusion detector, and a capillary viscometer. The measurement instrument and the measurement conditions were as described below.

Pump/autosampler: GPCmax available from VISCOTECH CO., LTD.

Guard column: SHODEX GF-7B

Column: two TOSOH GMPWXL columns connected in series were used

Detector: TDA302 available from VISCOTECH CO., LTD. (temperature in the system was maintained at 30° C.)

Solvent: aqueous solution of 60 mM sodium dihydrogen phosphate dihydrate and 20 mM disodium hydrogen phosphate dodecahydrate Flow rate: 0.5 mL/min Feeding amount: 100 μL The instrument was calibrated by using polyoxyethylene glycol (weight average molecular weight (Mw) 22396, differential refractive index (dn/dc)=0.132, solvent refractive index 1.33) as a standard sample.

In a case where the to-be-measured substance was a water-absorbing resin obtained by polymerizing monomer containing 99 mol % or more acrylic acid (salt), the measurement was performed on the assumption that the differential refractive index (dn/dc) of the polymer to be analyzed was 0.12. In a case where the to-be-measured substance was a copolymerized water-absorbing resin which contains a monomer other than acrylic acid (salt) in an amount of 1 mol % or more, the measurement was performed by measuring the value of the differential refractive index (dn/dc) inherent to that polymer in a solvent and using the obtained value. Furthermore, data of the refractive index, light scattering intensity, and viscosity were collected and analyzed with the use of Viscotek OmniSEC 3.1 (Registered Trademark) software. The weight average molecular weight (Mw) was calculated based on the data obtained from the refractive index and the light scattering intensity.

(f) Viscosity

Each fluid was prepared and viscosity was measured as disclosed below while referring to the content described in ISO 13503-1: 2003 "Recommended Practice for the Measurement of Viscous Properties of Completion Fluids".

(Viscosity in Ion Exchange Water)

0.084 g of a water absorbent material, such as a water absorbent resin and the like, was added to 70 g of ion exchange water. The mixture was stirred and dispersed with a homogenizer disperser. The entire dispersion was then transferred to the viscometer. The time at which the resin was added to the ion exchange water was considered the starting point, and viscosity up to 30 minutes thereafter was measured. The viscosity measuring apparatus and measurement conditions were the following.

Viscometer: manufactured by HAAKE (model number: VT550)

Viscometer jig: MV3

Shearing rate: 100 s$^{-1}$

Temperature: 25±0.3° C.

(Viscosity in Aqueous Physiological Saline Solution)

Measurement similar to those for ion exchange water was performed, other than adding 0.504 g of water absorbent material such as a water absorbent resin and the like to 70 g of aqueous 0.9 weight % sodium chloride solution.

Test Example 1

A water soluble aqueous unsaturated monomer solution was prepared by mixing together at once a solution prepared by dissolving 0.24 g of polyethyleneglycol diacrylate (average number of moles added of ethylene oxide: 9, molecular weight: 523) as an internal crosslinking agent to 332.4 g of acrylic acid, 12.3 g of aqueous 10.0 weight % trisodium diethylenetriamine pentaacetic acid solution, 285.3 g of aqueous solution of 48.5 weight % sodium hydroxide, and 301 g of deionized water. The temperature of the aqueous monomer solution at this time was 96° C.

Subsequently, 18.4 g of 3.0 weight % aqueous solution of sodium persulfate was added before the temperature of the aqueous monomer solution decreased. The mixture was immediately poured into a stainless steel vat container (bottom surface 340×340 mm, height 25 mm, inner surface: Teflon (registered trademark) coated) whose surface was heated to a temperature of 80° C. with a hot plate (manufactured by Iuchi Seieido Co., Ltd., NEO HOTPLATE H1-1000) in an open system.

Soon after the aqueous monomer solution was poured into the vat container, polymerization started. The polymerization progressed while the aqueous monomer solution generating water vapor, forming, expanding vertically and horizontally, and then the solution contracted to a size slightly larger than the stainless steel vat container. The expansion and contraction ended within about 1 minute. After three minutes, the water containing polymer (hydrogel) was retrieved. The series of operations were performed in a system opened to the atmosphere.

The resulting crosslinked hydrogel polymer (hydrogel) was crushed with a meat chopper (manufactured by Iizuka Kogyo Co., Ltd., MEAT-CHOPPER TYPE: 12VR-400KSOX, die pore size: 7.5 mm, number of pores: 24, die thickness 8 mm) to obtain a crushed crosslinked hydrogel polymer. For this operation, the amount of hydrogel added was about 350 g/min, and crushing was performed while adding deionized water adjusted to a temperature of 90° C. at 50 g/min concurrently with the addition of hydrogel.

The crushed crosslinked hydrogel polymer was spread on a stainless steel mesh with a mesh size of 850 μm and dried with hot air for 30 minutes at 190° C. The dried product obtained by the drying was pulverized using a roll mill (Inokuchi Giken Ltd., WML roll mill), and then classified using a JIS standard sieves with respective mesh sizes of 850 μm and 45 μm.

With the above-described operation, pulverized water absorbent resin particles having an uneven shape, with 97 weight % solid content, weight average particle diameter (D50) of 210 μm, and logarithmic standard deviation (σζ) of particle size distribution of 0.39 were obtained. Furthermore, water absorbent resin powder (1) was ultimately obtained by adding 0.5 parts by mass of Nippon AEROSIL's AEROSIL (registered trademark) 200 fumed silica to 100 parts by mass of the above-described water absorbent resin and mixing the mixture homogeneously.

Test Example 2

The roll mill (manufactured by Inokuchi Giken Ltd., WML roll mill) was adjusted so that the particle size of the resulting crushed product would be larger than the crushed product of Test Example 1, and fumed silica was not added. Other than the above, the same operation in Test Example 1 was performed to obtain pulverized water absorbent resin particles (2) having an uneven shape, with 97 weight % solid content, weight average particle diameter (D50) of 410 µm, and logarithmic standard deviation ($\sigma\zeta$) of particle size distribution of 0.37 were obtained.

Test Example 3

12.1 g of aqueous 48 weight % sodium hydroxide solution and 42.1 g of ion exchange water were placed in a polypropylene container (manufactured by Tokyo Glass Kikai Co., Ltd.) with a capacity of 250 mL. The mixture was stirred while cooling with ice. A mixture of 0.02 g of methylenebisacrylamide and 14.0 g of acrylic acid was slowly added thereto to prepare a reaction solution. The reaction solution was then stirred under reduced pressure and deaerated for 3 minutes. Subsequently, 1.7 g of aqueous 3% by mass potassium persulfate solution and 15 µL of tetramethylethylenediamine were added thereto while stirring. The resulting reaction solution was quickly transferred using a syringe into the following reaction container which had replaced with nitrogen gas therein, and was left standing for 15 hours in a dryer at 60° C. to obtain a disk-shaped gel. The above-described reaction container had a structure in which silicon rubber with a circular air hole was sandwiched between two sheets of glass plates, with the circumference thereof held with a clip.

The resulting gel was cut into several millimeter squares with a pair of scissors and placed on a stainless steel vat container. The gel was introduced into a reduced pressure dryer that was preheated to 150° C. and heated under normal pressure. After two hours from the introduction of the gel, the pressure in the dryer was reduced from normal pressure to reduced pressure to further dry the gel for 5 hours. The heating in the dryer was then discontinued. The gel was left standing for an additional 12 hours or more while maintaining the reduced pressure in the dryer. The dried product resulting from the drying was pulverized using a roll mill (manufactured by Inokuchi Giken Ltd., WML roll mill), and then classified using a JIS standard sieves with respective mesh sizes of 850 µm and 45 µm.

With the above-described operation, pulverized water absorbent resin particles (3) having an uneven shape, with 97 weight % solid content, weight average particle diameter (050) of 410 µm, and logarithmic standard deviation ($\sigma\zeta$) of particle size distribution of 0.37 were obtained.

Test Example 4

Other than the following change in the amount of substances used in polymerization, the same operation as Test Example 3 was performed to obtain pulverized water absorbent resin particles (4) having an uneven shape. Specifically, 14.3 g of aqueous 48 weight % sodium hydroxide solution and 17.1 g of ion exchange water were placed in a polypropylene container (manufactured by Tokyo Glass Kikai Co., Ltd.) with a capacity of 250 mL. The mixture was stirred while cooling with ice. A mixture of 0.001 g of methylenebisacrylamide and 16.5 g of acrylic acid was slowly added thereto to prepare a reaction solution. The reaction solution was then stirred under reduced pressure and deaerated for 3 minutes. Subsequently, 2.1 g of aqueous 3% by mass potassium persulfate solution and 17 µL of tetramethylethylenediamine were added thereto while stirring. The same operation as Test Example 3 was performed thereafter to obtain the water absorbent resin particles (4).

The pulverized water absorbent resin particles (4) had an uneven shape, with 97 weight % solid content, weight average particle diameter (050) of 410 µm, and logarithmic standard deviation ($\sigma\zeta$) of particle size distribution of 0.37.

Test Example 5

A reaction solution was prepared by dissolving 1.7 g of polyethyleneglycol diacrylate (average number of moles added of ethylene oxide: 9, molecular weight: 523) into 5500 g an aqueous solution of sodium acrylate (monomer concentration of 38% by mass) having a neutralization rate of 75 mole %. After the reaction solution was deaerated for minutes under a nitrogen gas atmosphere, the above-described reaction solution was supplied to a reactor, which included a double arm jacketed stainless kneader having an internal capacity of 10 L with two sigma blades and a lid. Nitrogen gas was blown into the reaction solution while maintaining the reaction solution temperature at 30° C., and the dissolved oxygen was then replaced with nitrogen so that the dissolved oxygen in the reaction system would be 1 ppm or less.

Subsequently, 29.8 g of aqueous 10% by mass solution of sodium persulfate and 21.8 g of aqueous 0.2% by mass aqueous solution of L-ascorbic acid were added while stirring the reaction solution, resulting in polymerization being initiated after about 1 minute. After 17 minutes from the initiation of the polymerization, peak polymerization temperature of 86° C. was exhibited. After 60 minutes from the initiation of the polymerization, a hydrogel polymer was retrieved.

The resulting hydrogel polymer was crushed into particles with a size of about 1 to 5 mm. The crushed hydrogel polymer was spread on a mesh with a 50 mesh (opening of 300 µm) and dried with hot air for 45 minutes at 180° C. to obtain a dried product.

The dried product was crushed using a roll mill (manufactured by Inokuchi Giken Ltd., WML roll mill), and then classified using a mesh with respective mesh sizes of 600 µm and 45 µm to obtain a pulverized water absorbent resin having an indeterminate shape with a weight average particle diameter (D50) of 210 µm. A water absorbent resin (5) was then obtained by adding 0.3 parts by mass of Nippon AEROSIL's AEROSIL (registered trademark) 200 fumed silica and 0.22 g of aqueous 45.0 weight % trisodium diethylenetriamine pentaacetic acid solution to 100 parts by mass of the resulting water absorbent resin and drying the mixture for 1 hour in a dryer at 60° C.

Test Example 6

A reaction solution was prepared by dissolving 1.7 g of polyethyleneglycol diacrylate (average number of moles added of ethylene oxide: 9, molecular weight: 523) into 5500 g of an aqueous solution of sodium acrylate (monomer concentration of 38% by mass) having a neutralization rate of 75 mole %. After the reaction solution was deaerated for minutes under nitrogen gas atmosphere, the above-described reaction solution was supplied to a reactor, which included a double arm jacketed stainless kneader having an internal capacity of 10 L with two sigma blades and a lid. Nitrogen gas was blown into the reaction solution while maintaining the reaction solution temperature at 30° C., and the dissolved oxygen was then replaced with nitrogen so that the dissolved oxygen in the reaction system would be 1 ppm or less.

Subsequently, 29.8 g of aqueous 10% by mass solution of sodium persulfate and 21.8 g of aqueous 0.2% by mass aqueous solution of L-ascorbic acid were added while stirring the reaction solution, resulting in polymerization being initiated after about 1 minute. After 17 minutes from the initiation of the polymerization, peak polymerization temperature of 86° C. was exhibited. After 60 minutes from the initiation of the polymerization, a hydrogel polymer was retrieved.

The resulting hydrogel polymer was crushed into particles with a size of about 1 to 5 mm. The crushed hydrogel polymer was spread on a mesh with a 50 mesh (opening of 300 µm) and dried with hot air for 45 minutes at 180° C. to obtain a dried product.

The dried product was crushed using a roll mill (manufactured by Inokuchi Giken Ltd., WML roll mill), and then classified using a mesh with respective mesh sizes of 850 µm and 45 µm to obtain a crushed water absorbent resin having an uneven shape. The CRC (fluid retention capacity (without pressure)) of water absorbent resin particles in physiological saline was 54 [g/g] and the weight average particle diameter (D50) was 410 µm.

3.62 parts by mass of an aqueous surface crosslinking agent solution consisting of 0.02 parts by mass of ethylene glycol diglycidyl ether, 0.3 parts by mass of 1,4-butanediol, 0.5 parts by mass of propylene glycol, and 2.8 parts by mass of water was then mixed with 100 parts by mass of the resulting water absorbent resin particles. The above-described mixture was heated for 40 minutes in a mortar mixer heated to 195° C. to obtain a surface crosslinked water absorbent resin.

Furthermore, water absorbent resin powder (0) was ultimately obtained by adding 0.3 parts by mass of Nippon AEROSIL's AEROSIL (registered trademark) 200 fumed silica and 0.1 g of aqueous 10 weight % trisodium diethylenetriamine pentaacetic acid solution to 100 parts by mass of the above-described water absorbent resin.

Test Example 7

A water absorbent resin (7) was obtained by performing the same operation as Test Example 5, except 0.3 parts by mass of AEROSIL (registered trademark) 200 was mixed without adding an aqueous trisodium diethylenetriamine pentaacetic acid solution as a chelating agent in Test Example 5 (water absorbent resin (5)).

The measurement results of fluid retention capacity, fluid retention capacity under pressure, amount of water soluble component and weight average molecular weight thereof, and viscosity, as well as the amount of chelating agent are shown in the following Table 1 for the polymers obtained in each of the above-described Test Example.

TABLE 1

| | Average particle diameter [µm] | Fluid retention capacity [g/g] | | Fluid retention capacity*) [g/g] | | pH soluble content [wt. %] | pH soluble content*) [wt. %] | Soluble content average molecular weight*) Mw |
|---|---|---|---|---|---|---|---|---|
| | | Ion exchange water | Physiological Saline | Ion exchange water | Physiological Saline | | | |
| Water absorbent resin (0) | 410 | 374 | 41 | 390 | 42 | 24 | 24 | 6.28 * 10$^5$ |
| Water absorbent resin (1) | 210 | 930 | 74 | 1040 | 76 | 46 | 47 | 1.09 * 10$^5$ |
| Water absorbent resin (2) | 410 | 934 | 71 | 1040 | 76 | 43 | 47 | 1.09 * 10$^5$ |
| Water absorbent resin (3) | 380 | 905 | 73 | 940 | 75 | — | 49 | 5.31 * 10$^5$ |
| Water absorbent resin (4) | 380 | 1169 | 81 | 1250 | 85 | — | 74 | 1.33 * 10$^5$ |
| Water absorbent resin (5) | 210 | 424 | 50 | 425 | 53 | 27 | 30 | 5.51 * 10$^5$ |
| Non-crosslinked polymer (6) | 350 | — | — | — | — | 94 | — | 2.08 * 10$^5$ |
| Water absorbent resin (7) | 210 | 428 | 50 | — | — | 27 | 30 | — |

| | Viscosity after 30 minutes [mPa · s] | | Viscosity after 24 hours at 80° C. [mPa · s] | | Amount of chelating agent (ppm) |
|---|---|---|---|---|---|
| | Ion exchange water | Physiological Saline | Ion exchange water | Physiological Saline | |
| Water absorbent resin (0) | 97 | 13 | 145 | 15 | 99 |
| Water absorbent resin (1) | 473 | 139 | 245 | 112 | 3000 |

TABLE 1-continued

| | | | | | |
|---|---|---|---|---|---|
| Water absorbent resin (2) | 598 | 103 | 248 | 118 | 3000 |
| Water absorbent resin (3) | 249 | 74 | — | — | 0 |
| Water absorbent resin (4) | 379 | 153 | — | — | 0 |
| Water absorbent resin (5) | 137 | 33 | 137 | 33 | 1000 |
| Non-crosslinked polymer (6) | 53 | 133 | 44 | 130 | 0 |
| Water absorbent resin (7) | 142 | 30 | 8 | 55 | 0 |

*)Measurement values for particles with a particle size of Pass 425 μm/ON 300 μm
Non-crosslinked polymer (6) corresponds to Nippon Shokubai Co., Ltd's Aquaric (registered trademark) FH-G.

The relationship between the amount of water absorbent resin used and viscosity (viscosity after 30 minutes) is the following. The results are shown in FIGS. 3 to 6.

TABLE 2

Relationship between the amount of water absorbent resin used and the viscosity (viscosity after 30 minutes)

Ion exchange water

| | Amount used (g) | | |
|---|---|---|---|
| | 0.042 | 0.084 | 0.168 |
| Water absorbent resin (0) | 21 | 97 | 920 |

Physiological Saline

| | Amount used (g) | | |
|---|---|---|---|
| | 0.504 | 1.008 | 1.512 |
| Water absorbent resin (0) | 13 | 224 | 2830 |

Ion exchange water

| | Amount used (g) | | |
|---|---|---|---|
| | 0.021 | 0.042 | 0.084 |
| Water absorbent resin (1) | 25 | 131 | 473 |

Physiological Saline

| | Amount used (g) | | | | |
|---|---|---|---|---|---|
| | 0.252 | 0.42 | 0.462 | 0.504 | 0.8399 |
| Water absorbent resin (1) | 17 | 59 | 81 | 139 | 630 |

Sand (sea sand) dispersion and precipitation tests were conducted for a water absorbent resin (1) and a non-crosslinked polymer (6). The results are shown in FIGS. 7 and 8. The sand (sea sand) used was 300 to 600 μm (30 to 50 mesh) sea sand manufactured by Wako Pure Chemical Industries, Ltd. 0.5 ppa (4.2 g) of sand was added to 70 g of viscosity evaluation solution and mixed by thoroughly shaking the container for 10 seconds (24° C.). FIG. 7 shows that water absorbent resin (1) remains dispersed after 3 hours, while the dispersion of non-crosslinked polymer (6) is not maintained. FIG. 8 shows a precipitation test with the amount of water absorbent resin (1) used changed so that the viscosity was 139 mPa·s, 81 mPa·s, and 59 mPa·s. It is understood that dispersion of sand is maintained when the viscosity is maintained at or above a given viscosity.

Heat Resistance Testing Method

<Test Under 80° C.>

As in the measurements of viscosity described in the above (Viscosity in ion exchange water) and (Viscosity in physiological saline solution), the dispersion of a water absorbent material such as a water absorbent resin and the like in ion exchange water or physiological saline was placed in a vial manufactured by Maruemu Corporation (model no. 8), capped and heated for a predetermined time at 80° C. in a hot air dryer.

<Test Under 110° C.>

As in the measurements of viscosity described in the above (Viscosity in ion exchange water) and (Viscosity in physiological saline solution), the dispersion of a water absorbent material such as a water absorbent resin and the like in ion exchange water or physiological saline was placed in a Big Boy Wide-mouth 100 ml (Teflon (registered trademark) super PFA bottle) manufactured by As One Corporation, capped and heated for a predetermined time at 110° C. in a physics and chemistry autoclave (model: MCS-3032S) manufactured by Alp corporation. Since the inside of the autoclave is pressurized, 4 holes of about 1 mm were provided on the container containing the sample as air vents. When the weight of the sample decreased after heating, ion exchange water was added to regain the state prior to heating. Meantime, when the weight increased, the viscosity was directly measured.

The relationship between the amount of chelating agent and the viscosity after a 80° C. heat resistance test (stable value after 2 minutes) is as disclosed below. Tests on the amount of chelating agent other than the amount of chelating agent of water absorbent resins (1) and (5) was conducted by preparing a test sample (water absorbent resin), to which the aqueous trisodium diethylenetriamine pentaacetic acid solution in Test Examples (1) and (5) was not added, and adding the amount of chelating agent at a condition amount in an absorbed liquid. The results are shown in FIGS. 9 to 12.

TABLE 3

Amount of chelating agent and viscosity after a 80° C. heat resistance test (stable value after 2 minutes)

(24 hours)

Ion exchange water

Amount of chelating agent (ppm: with respect to SAP)
Amount of SAP used 0.084 g

| | 0 | 100 | 1000 | 3000 |
|---|---|---|---|---|
| Water absorbent resin (1) | 8 | 201 | 212 | 208 |

Physiological Saline

Amount of chelating agent (ppm: with respect to SAP)
Amount of SAP used 0.504 g

| | 0 | 100 | 1000 | 3000 |
|---|---|---|---|---|
| Water absorbent resin (1) | 56 | 94 | 97 | 99 |

Ion exchange water

Amount of chelating agent (ppm: with respect to SAP)
Amount of SAP used 0.084 g

| | 0 | 100 | 1000 | 3000 |
|---|---|---|---|---|
| Water absorbent resin (5) | 8 | 145 | 136 | 134 |

Physiological Saline

Amount of chelating agent (ppm: with respect to SAP)
Amount of SAP used 0.504 g

| | 0 | 100 | 1000 | 3000 |
|---|---|---|---|---|
| Water absorbent resin (5) | 55 | 31 | 31 | 33 |

(96 hours)

Ion exchange water

Amount of chelating agent (ppm: with respect to SAP)
Amount of SAP used 0.084 g

| | 0 | 100 | 1000 | 3000 |
|---|---|---|---|---|
| Water absorbent resin (1) | 6 | 158 | 183 | 185 |

Physiological Saline

Amount of chelating agent (ppm: with respect to SAP)
Amount of SAP used 0.504 g

| | 0 | 100 | 1000 | 3000 |
|---|---|---|---|---|
| Water absorbent resin (1) | 17 | 85 | 91 | 90 |

Ion exchange water

Amount of chelating agent (ppm: with respect to SAP)
Amount of SAP used 0.084 g

| | 0 | 100 | 1000 | 3000 |
|---|---|---|---|---|
| Water absorbent resin (5) | 6 | 167 | 167 | 161 |

Physiological Saline

Amount of chelating agent (ppm: with respect to SAP)
Amount of SAP used 0.504 g

| | 0 | 100 | 1000 | 3000 |
|---|---|---|---|---|
| Water absorbent resin (5) | 10 | 45 | 44 | 42 |

The relationship between the amount of chelating agent and the viscosity after a 110° C. heat resistance test (stable value after 2 minutes) is as disclosed below. The results thereof are shown in FIGS. 13 to 16.

TABLE 4

Amount of chelating agent and viscosity after a 110° C. heat resistance test (stable value after 2 minutes)

(24 hours)

Ion exchange water

Amount of chelating agent (ppm: with respect to SAP)
Amount of SAP used 0.084 g

| | 0 | 100 | 1000 | 3000 |
|---|---|---|---|---|
| Water absorbent resin (1) | 16 | 80 | 105 | 105 |

Physiological Saline

Amount of chelating agent (ppm: with respect to SAP)
Amount of SAP used 0.504 g

| | 0 | 100 | 1000 | 3000 |
|---|---|---|---|---|
| Water absorbent resin (1) | 52 | 90 | 93 | 91 |

Ion exchange water

Amount of chelating agent (ppm: with respect to SAP)
Amount of SAP used 0.084 g

| | 0 | 100 | 1000 | 3000 |
|---|---|---|---|---|
| Water absorbent resin (5) | 21 | 126 | 162 | 164 |

TABLE 4-continued

Amount of chelating agent and viscosity after a 110° C.
heat resistance test (stable value after 2 minutes)

Physiological Saline

Amount of chelating agent
(ppm: with respect to SAP)
Amount of SAP used 0.504 g

| | 0 | 100 | 1000 | 3000 |
|---|---|---|---|---|
| Water absorbent resin (5) | 79 | 70 | 76 | 79 |

(72 hours)

Ion exchange water

Amount of chelating agent
(ppm: with respect to SAP)
Amount of SAP used 0.084 g

| | 0 | 100 | 1000 | 3000 |
|---|---|---|---|---|
| Water absorbent resin (1) | 9 | 15 | 67 | 65 |

Physiological Saline

Amount of chelating agent
(ppm: with respect to SAP)
Amount of SAP used 0.504 g

| | 0 | 100 | 1000 | 3000 |
|---|---|---|---|---|
| Water absorbent resin (1) | 28 | 73 | 77 | 81 |

Ion exchange water

Amount of chelating agent
(ppm: with respect to SAP)
Amount of SAP used 0.084 g

| | 0 | 100 | 1000 | 3000 |
|---|---|---|---|---|
| Water absorbent resin (5) | 7 | 15 | 78 | 79 |

Physiological Saline

Amount of chelating agent
(ppm: with respect to SAP)
Amount of SAP used 0.504 g

| | 0 | 100 | 1000 | 3000 |
|---|---|---|---|---|
| Water absorbent resin (5) | 28 | 75 | 78 | 80 |

The relationship between the concentration of absorbed liquid (aqueous NaCl solution or aqueous CaCl$_2$ solution) i.e., the salt concentration of the absorbed liquid, and the fluid retention capacity is as follows. The results thereof are shown in FIGS. 17 and 18.

TABLE 5

Measurement of fluid retention capacity

Aqueous NaCl solution

| Absorbed Liquid Concentration [% by mass] | Water absorbent resin (1) fluid retention capacity [g/g] | Water absorbent resin (0) fluid retention capacity [g/g] |
|---|---|---|
| 0.05 | 226 | 134 |
| 0.1 | 175 | 103 |
| 0.5 | 89 | 53 |
| 0.9 | 74 | 41 |
| 1.5 | 58 | 34 |
| 2 | 51 | 29 |

TABLE 6

Measurement of fluid retention capacity

Aqueous CaCl$_2$ solution

| Absorbed Liquid Concentration [% by mass] | Water absorbent resin (1) fluid retention capacity [g/g] | Water absorbent resin (0) fluid retention capacity [g/g] |
|---|---|---|
| 0.05 | 148 | 101 |
| 0.075 | 120 | 81 |
| 0.1 | 106 | 71 |
| 0.2 | 57 | 39 |
| 0.3 | 30 | 26 |
| 0.5 | 16 | 13 |

As can be understood from the above-described experimental results, the viscosities of water absorbent resins after 30 minutes vary depending on the fluid retention capacity of the water absorbent resin used and the fluid medium used (e.g., fluid retention capacity, ion exchange water, and physiological saline in Tables 1 to 4). Further, the fluid retention capacities of water absorbent resins themselves vary depending on the components in the fluid medium used (e.g., aqueous NaCl solution and aqueous CaCl$_2$ solution in Tables 5 and 6). The viscosity of water absorbent resins can also vary depending on the temperature (e.g., viscosity after 30 minutes (normal temperature), viscosity after 80° C. heat resistance test, and viscosity after 110° C. heat resistance test in Tables 1 to 4). For a fracturing fluid in a hydraulic fracturing method that utilizes water such as lake water or river water in the area, it is generally difficult to predict the suitable water absorbent material in advance due to various such factors. Meanwhile, the present invention provides a method of determining a water absorbent material that enables a proppant particle to be stably dispersed (suspended) in a fracturing fluid. Further, heat resistance can be enhanced by using a chelating agent. The present invention provides a fracturing fluid that is suitable for a hydraulic fracturing method.

As described above, the present invention is exemplified by the use of its preferred embodiments. However, it is understood that the scope of the present invention should be interpreted solely based on the Claims. It is also understood that any patent, patent application, and references cited herein should be incorporated herein by reference in the same manner as the contents are specifically described herein. The present application claims priority to Japanese Patent Application No. 2015-149654 filed on Jul. 29, 2015. The entire content of these applications is incorporated herein by reference.

INDUSTRIAL APPLICABILITY

The inventors have discovered a novel acrylic acid crosslinked polymer and use thereof in a fluid (fracturing fluid) used in hydraulic fracturing of a stratum. Thus, the present invention is effective in the field of hydraulic fracturing of a stratum.

The invention claimed is:

1. An acrylic acid crosslinked polymer in which acrylic acid (salt) has been polymerized as a main component of a monomer, wherein a fluid retention capacity of the polymer in physiological saline is 40 g/g or greater, a fluid retention capacity of the polymer in ion exchange water is 300 g/g or greater, and an amount of a soluble content of the polymer relative to 0.9 weight % of aqueous sodium chloride solution is 40 weight % or greater and less than 95 weight %
wherein the acrylic acid crosslinked polymer farther satisfies at least one selected from the following (a), (b) and (c):
(a) wherein a weight average molecular weight of the soluble content is one million Dalton or greater,
(b) wherein a viscosity upon a 0.12 weight % dispersion of the polymer in ion exchange water is 100 mPa·s or greater and/or a viscosity upon a 0.72 weight % dispersion of the polymer in physiological saline is 20 mPa·s or greater, and
(c) wherein an amount of variation in viscosity over time exhibits at or below a certain value of any of (1) to (4) below:
(1) an amount of variation from viscosity after 24 hours to viscosity after 96 hours in a 80° C. heat tolerance test using ion exchange water of 15% or less;
(2) an amount of variation from viscosity after 24 hours to viscosity after 96 hours in a 80° C. heat tolerance test using physiological saline of 15% or less;
(3) an amount of variation from viscosity' after 24 hours to viscosity after 72 hours In a 110° C. heat tolerance test in ion exchange water of 15% or less; and
(4) an amount of variation from viscosity after 24 hours to viscosity after 72 hours in a 110° C. heat tolerance test in physiological saline of 15% or less.

2. The acrylic acid crosslinked polymer of claim 1, wherein the fluid retention capacity in physiological saline is 60 g/g or greater and/or the fluid retention capacity in ion exchange water is 600 g/g or greater.

3. The acrylic acid crosslinked polymer according to claim 1, wherein at least one selected from the amount of soluble content, the weight average molecular weight of the soluble content, the fluid retention capacity in physiological saline and the fluid retention capacity in ion exchange water is a value of the acrylic acid crosslinked polymer with a particle size greater than 300 μm and less than 425 μm.

4. The acrylic acid crosslinked polymer according to claim 1, wherein the acrylic acid crosslinked polymer is a particle with an average particle diameter (D50) of 10 μm or greater.

5. The acrylic acid crosslinked polymer of claim 1, wherein a neutralization rate with respect to an acid group of the monomer is 10 to 100 mole %.

6. The acrylic acid crosslinked polymer of claim 1, wherein a neutralization rate of the acrylic acid crosslinked polymer is greater than 75 mole %.

7. The acrylic acid crosslinked polymer of claim 1, further comprising a chelating agent.

8. The acrylic acid crosslinked polymer of claim 7, wherein the chelating agent is a compound selected from the group consisting of amino multivalent carboxylic acid, organic multivalent phosphoric acid, inorganic multivalent phosphoric acid, and amino multivalent phosphoric acid, wherein a molecular weight of the chelating agent is 100 to 5000, and the chelating agent is a water soluble chelating agent.

9. The acrylic acid crosslinked polymer of claim 7, wherein the chelating agent is selected from the group consisting of diethylenetriamine pentaacetic acid, triethylenetetraamine hexaacetic acid, and salts thereof.

10. The acrylic acid crosslinked polymer of claim 7, wherein the chelating agent is 0.01 weight % or greater with respect to the polymer in a water absorbent material.

11. The acrylic acid crosslinked polymer of claim 7, wherein the chelating agent is 0.1 weight % or greater.

12. The acrylic acid crosslinked polymer of claim 1, further comprising an α-hydroxycarboxylic acid compound.

13. The acrylic acid crosslinked polymer of claim 1, wherein the polymerization has been started with a temperature of an aqueous monomer solution at 35° C. or more and the upper limit is the boiling point of the solution.

14. The acrylic acid crosslinked polymer of claim 1, wherein polymerization has been carried out in a monomer concentration in an aqueous monomer solution of 40 weight % or more and the upper limit is the saturated concentration of the monomer.

15. The acrylic acid crosslinked polymer of claim 1, wherein a degree of an increase in a solid content concentration defined by the following formula (2) is 1 weight % or more, (Degree of an increase in a solid content(weight %))=(Solid content concentration of a hydrogel after polymerization(weight %))−(Solid content concentration of an aqueous monomer solution (weight %))  Formula (2).

16. The acrylic acid crosslinked polymer of claim 1, being further surface crosslinked.

17. The acrylic acid crosslinked polymer of claim 1, wherein an absorption against pressure (AAP) of the polymer is 25 g/g or greater.

18. The acrylic acid crosslinked polymer of claim 1, wherein a weight average particle diameter (D50) of the polymer is 200 to 600 μm, a percentage of particles having a particle size less than 150 μm is 10 weight % or less, a ratio of particles with a particle size of 850 μm or greater is 5 weight % or less, and a logarithmic standard deviation (at) of particle size distribution is 0.20 to 0.50.

* * * * *